US010367476B2

(12) United States Patent
Ricci et al.

(10) Patent No.: US 10,367,476 B2
(45) Date of Patent: Jul. 30, 2019

(54) METHOD AND SYSTEM FOR SIGNAL DECOMPOSITION, ANALYSIS AND RECONSTRUCTION

(71) Applicant: Vios Medical, Inc., St. Paul, MN (US)

(72) Inventors: Carlos A. Ricci, Apple Valley, MN (US); Vladimir V. Kovtun, Inver Grove Heights, MN (US)

(73) Assignee: Vios Medical, Inc., Woodbury, MN (US)

( * ) Notice: Subject to any disclaimer, the term of this patent is extended or adjusted under 35 U.S.C. 154(b) by 0 days.

(21) Appl. No.: 15/676,891

(22) Filed: Aug. 14, 2017

(65) Prior Publication Data
US 2018/0166089 A1 Jun. 14, 2018

Related U.S. Application Data

(60) Continuation of application No. 15/132,914, filed on Apr. 19, 2016, now Pat. No. 9,734,838, which is a
(Continued)

(51) Int. Cl.
*G10L 19/26* (2013.01)
*H03H 17/02* (2006.01)
(Continued)

(52) U.S. Cl.
CPC ....... *H03H 17/0248* (2013.01); *A61B 5/0432* (2013.01); *G10L 19/26* (2013.01);
(Continued)

(58) Field of Classification Search
CPC ........... G06K 9/00496; G06K 9/00503; G06K 9/00501; G06K 9/005016; G06K 9/00523;
(Continued)

(56) References Cited

U.S. PATENT DOCUMENTS 3,819,920 A 6/1974 Goldfischer
3,993,862 A 11/1976 Karr
(Continued)

OTHER PUBLICATIONS

Bracewell, Ronald N., "The Fourier Transform and its Applications (Table of Contents, Index Only)", 2000, Publisher: McGraw-Hill.
(Continued)

*Primary Examiner* — Dwayne D Bost
*Assistant Examiner* — Stephen M Brinich
(74) *Attorney, Agent, or Firm* — Fish & Richardson P.C.

(57) ABSTRACT

A system and method for representing quasi-periodic waveforms, for example, representing a plurality of limited decompositions of the quasi-periodic waveform. Each decomposition includes a first and second amplitude value and at least one time value. In some embodiments, each of the decompositions is phase adjusted such that the arithmetic sum of the plurality of limited decompositions reconstructs the quasi-periodic waveform. Data-structure attributes are created and used to reconstruct the quasi-periodic waveform. Features of the quasi-periodic wave are tracked using pattern-recognition techniques. The fundamental rate of the signal (e.g., heartbeat) can vary widely, for example by a factor of 2-3 or more from the lowest to highest frequency. To get quarter-phase representations of a component (e.g., lowest frequency "rate" component) that varies over time (by a factor of two to three) many overlapping filters use bandpass and overlap parameters that allow tracking the component's frequency version on changing quarter-phase basis.

20 Claims, 22 Drawing Sheets

Related U.S. Application Data division of application No. 14/217,317, filed on Mar. 17, 2014, now Pat. No. 9,319,028.

(60) Provisional application No. 61/801,292, filed on Mar. 15, 2013.

(51) Int. Cl.
*A61B 5/0432* (2006.01)
*G01V 1/28* (2006.01)

(52) U.S. Cl.
CPC .... *H03H 17/0201* (2013.01); *H03H 17/0266* (2013.01); *G01V 1/28* (2013.01); *G01V 2210/43* (2013.01)

(58) Field of Classification Search
CPC .............. G06K 9/0053; H04L 27/0004; H04L 27/2618; H04L 25/022; H04L 27/2602; G10L 19/02; H03M 3/468
USPC ................ 704/205–206, 219–220, 267–268; 455/303–307; 370/210
See application file for complete search history.

(56) References Cited

U.S. PATENT DOCUMENTS

| | | | |
|---|---|---|---|
| 4,193,393 A | 3/1980 | Schlager |
| 4,251,831 A | 2/1981 | Kamath |
| 4,314,105 A | 2/1982 | Mozer |
| 4,461,022 A | 7/1984 | Slagley |
| 4,633,884 A | 1/1987 | Imai et al. |
| 4,680,797 A | 7/1987 | Benke |
| 4,736,295 A | 4/1988 | Lachiver et al. |
| 5,115,240 A | 5/1992 | Fujiwara et al. |
| 5,230,038 A | 7/1993 | Fielder et al. |
| 5,392,044 A | 2/1995 | Kotzin et al. |
| 5,486,867 A | 1/1996 | Hsu et al. |
| 5,730,142 A | 3/1998 | Sun et al. |
| 5,749,367 A | 5/1998 | Gamlyn et al. |
| 5,778,881 A | 7/1998 | Sun et al. |
| 5,828,995 A | 10/1998 | Satyamurti et al. |
| 6,020,840 A | 2/2000 | Ong |
| 6,389,308 B1 | 5/2002 | Shusterman |
| 6,475,245 B2 | 11/2002 | Gersho et al. |
| 6,510,339 B2 | 1/2003 | Kovtun et al. |
| 6,512,944 B1 | 1/2003 | Kovtun et al. |
| 6,791,482 B2 | 9/2004 | Koyanagi |
| 6,914,935 B2 | 7/2005 | Eklof |
| 6,925,324 B2 | 8/2005 | Shusterman |
| 7,054,792 B2 | 5/2006 | Frei et al. |
| 7,058,548 B2 | 6/2006 | Pupalaikis et al. |
| 7,088,276 B1 | 8/2006 | Wegener |
| 7,254,187 B2 | 8/2007 | Mohan et al. |
| 7,640,055 B2 | 12/2009 | Geva et al. |
| 7,706,992 B2 | 4/2010 | Ricci et al. |
| 7,912,378 B2 | 3/2011 | Tian et al. |
| 2008/0015452 A1 | 1/2008 | Ricci et al. |

OTHER PUBLICATIONS

Cappe, Olivier, et al., "Inference in Hidden Markov Models (Table of Contents, Index Only)", 2005, Publisher: Springer.

Cetin, A. Enis, et al., "Compression of Digital Biomedical Signals", "The Biomedical Engineering Handbook: Second Edition. Joseph D. Bonzino, Ed. CRC Press LLC", 2000, vol. Chapter 54.

Chen, Ying-Jui, et al., "Multiplierless Approximations of Transforms with Adder Constraing", "IEEE Signal Processing Letters ", Nov. 2002, pp. 344-347, vol. 9, No. 11.

Duda, Richard O., et al., "Pattern Classification, Second Ed. (Table of Contents, Index Only)", 2001, Publisher: John Wiley & Sons, Inc.

Elliott, Richard J., et al., "Hidden Markov Models (Table of Contents, Index Only)", 1995, Publisher: Springer-Verlag.

Fliege, N. J., "Multirate Digital Signal Processing (Table of Contents, Index Only)", 1994, Publisher: Wiley.

Golub, Gene H., et al., "Matrix Computations, Third Ed. (Table of Contents, Index Only)", 1996, Publisher: Hopkins.

Kotteri, K., et al., "Design of Multiplierless, High-Performance, Wavelet Filter Banks with Image Compression Applications", "IEEE Transactions on Circuits and Systems,", Mar. 2004, pp. 483-494, vol. 51, No. 3.

Macdonald, Iain L., et al., "Hidden Markov and Other Models for Discrete-valued Time Series (Table of Contents, Index Only)", 1997, Publisher: Chapman.

Openheim, Alan V., et al., "Discrete-Time Signal Processing, Second Ed. (Table of Contents, Index Only)", 1999, Publisher: Wiley.

Ozaktas, Haldun M., et al., "The Fractional Fourier Transform (Table of Contents, Index Only)", 2001, Publisher: Wiley.

Stoica, Petre, et al., "Spectral Analysis of Signals (Table of Contents, Index Only)", 2005, Publisher: Prentice-Hall.

Strang, Gilbert, et al., "Wavelets and Filter Banks (Table of Contents, Index Only)", 1997, Publisher: Wellesley.

Vapnik, Vladimir N., "The Nature of Statistical Learning Theory, Second Ed. (Table of Contents, Index Only)", 2000, Publisher: Springer.

Vetterli, Martin, et al., "Wavelets and Subband Coding (Table of Contents, Index Only)", 1995, Publisher: Prentice-Hall.

Xue, Qiuzhen, et al., "Late Potential Recognition by Artificial Neural Networks", "IEEE Trans Bio Eng", 1997, pp. 132-143, vol. 44.

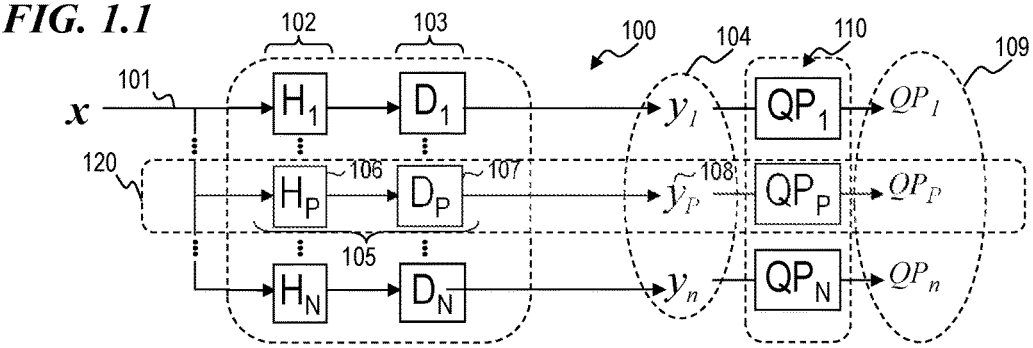
FIG. 1.1
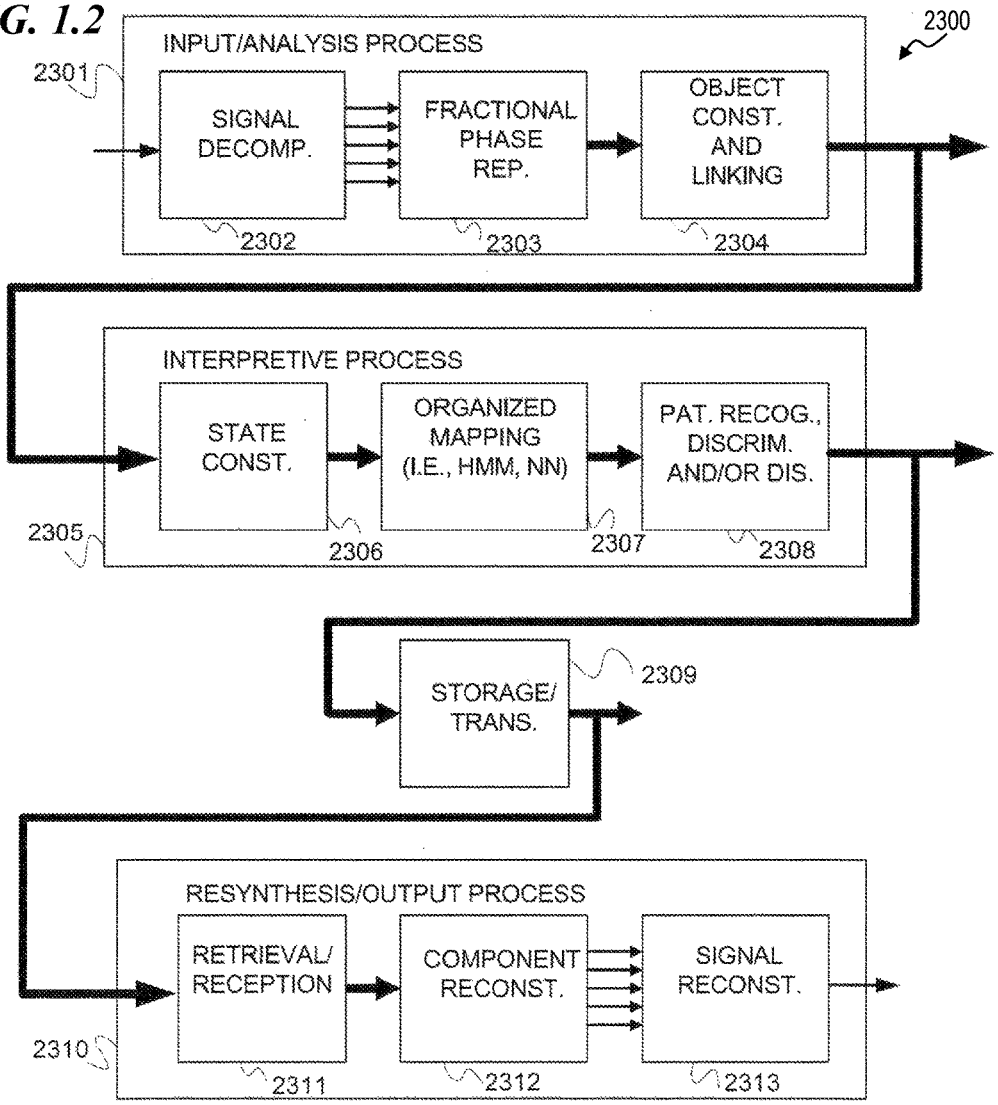
FIG. 1.2

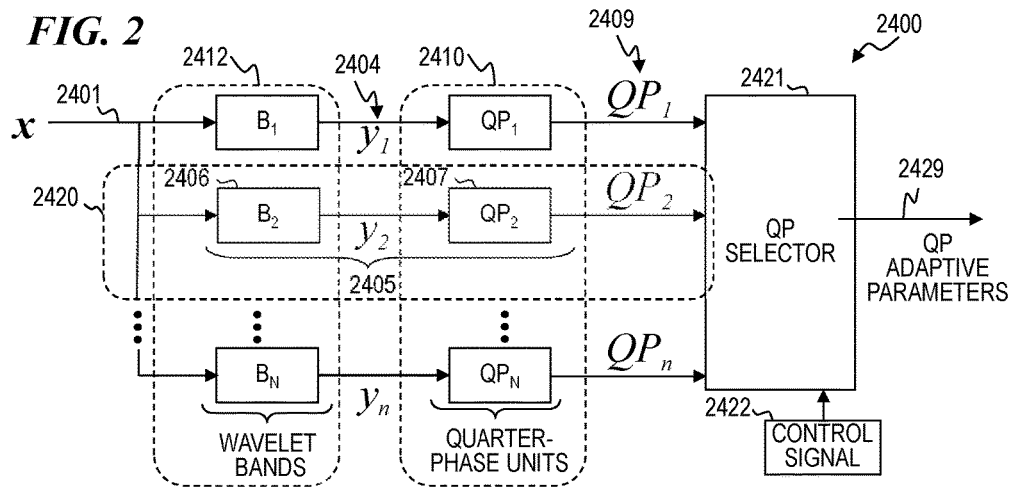
FIG. 2
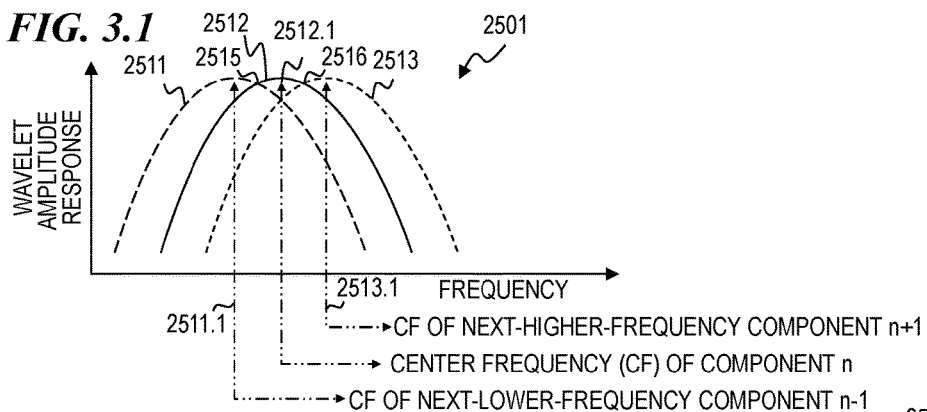
FIG. 3.1
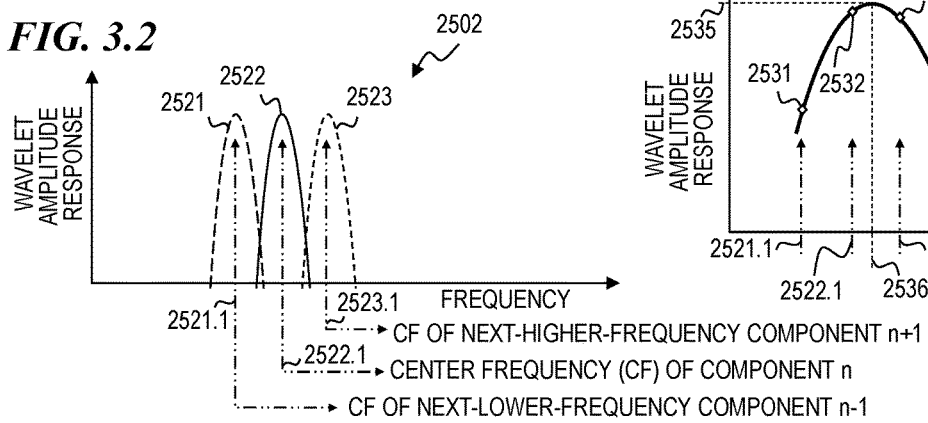
FIG. 3.2
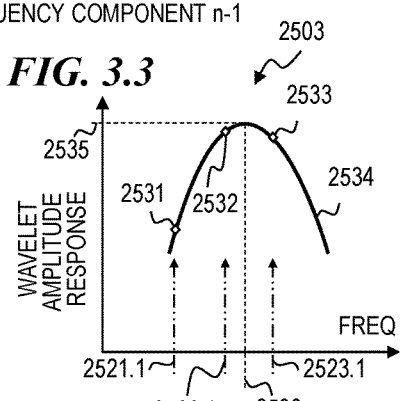
FIG. 3.3

| r | R(BRM) | $f_A$(Hz) | $K_r$ |
|---|---|---|---|
| 1 | 28.1477 | 0.4691 | 200 |
| 2 | 29.3206 | 0.4887 | 192 |
| 3 | 30.2666 | 0.5044 | 186 |
| 4 | 31.6271 | 0.5271 | 178 |
|  | 32.7305 | 0.5455 | 172 |
| · | 34.3273 | 0.5721 | 164 |
| · | 35.6311 | 0.5939 | 158 |
| · | 37.0378 | 0.6173 | 152 |
|  | 38.5601 | 0.6427 | 146 |
|  | 39.6465 | 0.6608 | 142 |
|  | 41.3959 | 0.6899 | 136 |
|  | 43.3068 | 0.7218 | 130 |
|  | 44.6819 | 0.7447 | 126 |
|  | 46.1472 | 0.7691 | 122 |
|  | 48.5346 | 0.8089 | 116 |
|  | 50.2683 | 0.8378 | 112 |
|  | 52.1305 | 0.8688 | 108 |
|  | 54.1360 | 0.9023 | 104 |
|  | 56.3019 | 0.9384 | 100 |
|  | 58.6484 | 0.9775 | 96 |
|  | 61.1990 | 1.0200 | 92 |
|  | 62.5593 | 1.0427 | 90 |
|  | 65.4699 | 1.0912 | 86 |
|  | 68.6644 | 1.1444 | 82 |
|  | 70.3816 | 1.1730 | 80 |
|  | 74.0870 | 1.2348 | 76 |
|  | 76.0900 | 1.2682 | 74 |
|  | 80.4395 | 1.3407 | 70 |
|  | 82.8063 | 1.3801 | 68 |
|  | 85.3165 | 1.4219 | 66 |
|  | 90.8229 | 1.5137 | 62 |
|  | 93.8516 | 1.5642 | 60 |
|  | 97.0892 | 1.6182 | 58 |
|  | 100.5582 | 1.6760 | 56 |
|  | 104.2843 | 1.7381 | 54 |
|  | 108.2972 | 1.8050 | 52 |
|  | 112.6313 | 1.8772 | 50 |
|  | 117.3267 | 1.9554 | 48 |
|  | 122.4307 | 2.0405 | 46 |
|  | 127.9989 | 2.1333 | 44 |
|  | 134.0978 | 2.2350 | 42 |
|  | 140.8070 | 2.3468 | 40 |
|  | 148.2230 | 2.4704 | 38 |
| · | 156.4636 | 2.6077 | 36 |
| · | 165.6745 | 2.7612 | 34 |
| · | 176.0379 | 2.9340 | 32 |
| 47 | 187.7843 | 3.1297 | 30 |
| 48 | 201.2106 | 3.3535 | 28 |

Function [Lqp, iqp, aqp, Msem] = getCmpQp (x)

% computed parameters
Lx = length (x) ;
% determine initial state
if     real (x(1)) >= 0 && imag (x(1)) <  0
   Lqps = 1;  % A state
elseif real (x(1)) >= 0 && imag (x(1)) >= 0
   Lqps = 2;  % B state
elseif real (x(1)) <   0 && imag (x(1)) >= 0
   Lqps = 3;  % C state
elseif real (x(1)) <   0 && imag (x(1)) >  0
   Lqps = 4;  % D state
end
aqps = 0;
iqps = 0;

% detect QP transitions
aqp = zeros (Lx, 1);   % QP amp
iqp = zeros (Lx, 1);   % QP index
Lqp = zeros (Lx, 1);   % QP label
nqp = 0;
if nargout > 3, Msem = Zeros (Lx,3); end
fUpdate = false;
for ix = 2: Lx
   if   Lqps == 4 && real (x(ix)) >= 0 && real (x(ix-1)) < 0
      Lqps = 1; % D -> A transition
      aqps = -imag (x(ix));
      fUpdate = true;
   elseif Lqps == 1 && imag (x(ix)) >= 0 && imag (x(ix-1)) < 0
      Lqps = 2; % A -> B transition
      aqps = real (x(ix));
      fUpdate = true;
   elseif Lqps == 2 && real (x(ix)) <= 0 && real (x(ix-1)) > 0
      Lqps = 3; % B -> C transition
      aqps = imag (x(ix));
       fUpdate = true;

```
    elseif Lqps == 3 && imag (x(ix)) <= 0 && imag (x(ix-1)) > 0
      Lqps = 4; % C -> D transition
      aqps = -real (x(ix));
      fUpdate = true;

end
    if fUpdate
      fUpdate = false;
      iqps = ix;
      nqp = nqp + 1;
      aqp (nqp) = aqps;
      iqp (nqp) = iqps;
      Lqp (nqp) = Lqps;
    end
      if nargout > 3, Msem (ix, :) = [Lqps, aqps, iqps]; end
end
apq = apq (1 : nqp);
iqp = iqp (1 : nqp);
Lqp = lqp (1 : npq);

return
```

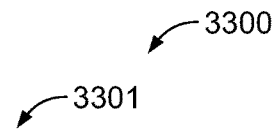

Function [Lqp, iqp, aqp, Msem] = getCmpQpltp (x)

% Computed parameters
Lx = length (x);

% determine initial state
if      real (x(1)) >= 0 && imag (x(1)) < 0
   Lqps = 1; % A State
elseif real (x(1)) >= 0 && imag (x(1)) >= 0
   Lqps = 2; % B State
elseif real (x(1)) <  0 && imag (x(1)) >= 0
   Lqps = 3; % C State
elseif real (x(1)) <  0 && imag (x(1)) <  0
   Lqps = 4; % D State
end
aqps = 0;
iqps = 0;

% detect QP transitions
aqp = zeros (Lx,1);  % QP amp
iqp = zeros (Lx,1);  % QP index
Lqp = zeros (Lx,1);  % QP label
nqp = 0;
if nargout > 3, Msem = zeros (Lx,3); end
fUpdate = false;

FIG. 11.2

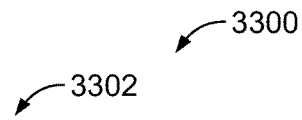

```
                                                              /-3300
                                                         /-3302
for ix = 2 : Lx
    if       Lqps == 4 && real (x(ix)) >= 0 && real (x(ix-1)) < 0
        Lqps = 1; % D -> A transition
        i0f = xintcpti (real (x(ix-1)) ,real (x(ix)));
        aqps = lintrp (-imag (x(ix-1)) ,-imag (x(ix)) ,i0f);
        fupdate = true;
    elseif Lqps == 1 && imag (x(ix)) >= 0 && imag (x(ix-1)) < 0
        Lqps = 1; % A -> B transition
        i0f = xintcpti (imag (x(ix-1)) ,imag (x(ix)));
        aqps = lintrp (real (x(ix-1)) ,real (x(ix)) ,i0f);
        fupdate = true;
    elseif Lqps == 2 && real (x(ix)) <= 0 && real (x(ix-1)) > 0
        Lqps = 3; % B -> C transition
        i0f = xintcpti (real (x(ix-1)) ,real (x(ix)));
        aqps = lintrp (imag (x(ix-1)) ,imag (x(ix)) ,i0f);
        fupdate = true;
    elseif Lqps == 3 && imag (x(ix)) <= 0 && real (x(ix-1)) > 0
        Lqps = 4; % C -> D transition
        i0f = xintcpti (imag (x(ix-1)) ,imag (x(ix)));
        aqps = lintrp (-real (x(ix-1)) ,-real (x(ix)) ,i0f);
        fupdate = true;
    end
    if fUpdate
        iqps = ix -1 + i0f;
        fUpdate = false;
        nqp = nqp + 1;

apq (nqp) = aqps;
        iqp (nqp) = iqps;
        Lqp (nqp) = Lqps;
    end
    if nargout > 3, Msem (ix, :) = [Lqps, aqps, iqps]; end
end
```

```
apq = aqp (1: npq);
iqp = iqp (1 : nqp);
Lqp = Lqp (1 : nqp);

return function I0f = xintcpti (y1, y2)

% fraction of sample index to zeroc crossing right of y1 i0f = -y1/ (y2 - y1);

return function yi = lintrp (y1, y2, i0f)

yi = y1 + (y2 - Y1) *i0f;

return
```

```
function sObj = getTfaQp (X, ITP)

if nargin < 2
      ITP = false;
end

Nb = size (x, 2);
for ib = 1 :Nb
     if ~ITP
         [Lqp, iqp, aqp] = getCmpQp (X(:, ib));
     else
         [Lqp, iqp, aqp] = getCmpQpltp (x(:, ib));
     end
     sObj (ib) .Lqp = Lqp;
     sObj (ib) .iqp = iqp;
     sObj (ib) .aqp = aqp;
end return
```

```
Function sQpCmp = trkMxQpA(sObj, Lx)

% initialize states
Nb = length (sObj);
aqpSt = arrayfun (@(x) x.aqp (1), sObj);    % qp amplitudes
iqpSt  = arrayfun (@(x) x.iqp(1), sObj);    % qp time indices
LqpSt = arrayfun (@(x) x.Lqp(1), sObj);     % qp labels
nqpSt = zeros (Nb, 1);  % qp counter for ea component band
NqpSt = arrayfun (@(x) length(x.iqp), sObj). ' ;   % total #qp's % initialize tracker
abmx = zeros (Lx, 1);  % tracked max amp
ibmx = zeros (Lx, 1);   % corresponding tracked band index
Lbmx = zeros (Lx, 1);  % corresponding tracked qp label
ixqp = zeros (Lx, 1);
nqp = 1;
[abmx(1), ibmx(1)] = max(aqpst);
%ixIni = min (aqpst) + 1;
for ix = 1:Lx
    fQpUp = ix >= iqpSt; % detect bands with qp update
    if any (fQpUp)
        % update qp counter(s)
        nqpSt(fQpUp) = min(nqpSt(fQpUp)+1, NqpSt(fQpUp));

% update states
        nbQpUp = find(fQpUp);
        Nup = length(nbQpUp);
        for iup = 1:Nup
            ib = nbQpUp(iup);                        % band to update
            aqpSt(ib) = sObj(ib).aqp(nqpSt (ib));    % update aqp state
            iqpSt(ib) = sObj(ib).iqp(nqpSt(ib));     % update iqp state
            LqpSt:.(ib) = sObj(ib).Lqp(nqpSt(ib));   % update Lqp state
        end
```

```
% update tracking
[abmxi, ibmxi ] = max(aqpSt);
if fQpUp(ibmxi) I I ibmxi ~= ibmx(nqp)
        % max band is a band that updated OR max @ new band
        nqp = nqp + 1;
        abmx(nqp) = abmxi;
        ibmx(nqp) = ibmxi;
        Lbmx(nqp) = LqpSt(ibmxi);
        ixqp (nqp) = ix;
    end
  end
end
sQpCmp.aqp = abmx(1:nqp) ;
sQpCmp.ibqp = ibmx(1:nqp);
sQpCmp.Lqp = Lbmx (1:nqp);
sQpCmp.iqp = ixqp(1:nqp);
return
```

*FIG. 13 (Cont.)*

```
                                                            ⟵ 3600
function sObj = flpsQpA (sObj, T, No, fan)

% fan = ana;ysis freq = 1/4 * #QP' s/sec
wQP = round(T * 4*fan);  % per-band time width in #QP's Nb = length(sObj);
for ib = 1:Nb
    sObj (ib) .aqpm = flpsfilt(sObj (ib) .aqp,1,0,1,0,1,wQP(ib),No);
end return
```

*FIG. 14*

←3700
←3701 function [sQpCmp, sQpCmpm] = trkMxQpAGrd(sObj, Lx, Ngrd)

% initialize states: "current" info for each component band
Nb = length (sObj) ;
aqpmSt = arrayfun (@(x) x.aqpm (1), sObj);   %MA qp amplitudes
aqpSt = arrayfun (@(x) x.aqp (1), sObj);     % qp amplitudes
iqpSt  = arrayfun (@(x) x.iqp(1), sObj);     % qp time indices
LqpSt = arrayfun (@(x) x.Lqp(1), sObj);      % qp labels
nqpSt = zeros (Nb, 1);  % qp counter for ea component band
NqpSt = arrayfun (@(x) length(x.iqp) ,sObj). ' ;   % total #qp's % initialize tracker
ammx = zeros (Lx, 1);   % tracked max MA amp
immx = zeros (Lx, 1);   % corresponding tracked band index
imqp = zeros (Lx, 1);   % time index of qp @ update point
nqpm = 1;
imqp (1) = 1;
%
ambx = zeros (Lx,1);    % tracked max amp over guard band
ibmx = zeros (Lx,1);    % corresponding tracked band index
nqmx = zeros (Lx,1);    % qp #count for tracked band (aux information)
                        % e.g use sObj (ibmx(ii)) .aqp(nqmx(ii))
Lbmx = zeros (Lx,1);    % corresponding tracked qp label
ixqp = zeros (Lx,1);    % time index of qp @ update point
nqp = 1:                % tracking update counter
ixqp(1) = 1;
% determine guard-band (GB) center+range
[ammx(1), immx(1)] = max (aqpSt (ibnd));  % center of GB
iL = max(1, immx(1) - Ngrd);
iH = min(Nb, immx(1) + Ngrd);
ibnd = iL : iH;                                        % GB range
% determine main max-amp within GB
[ambx(1), nbmx] = max(aqpSt (ibnd));
ibmx(1) = ibnd(nbmx);
nqmx(1) = nqpSt(inmx(1));
Lnmx(1) = LqpSt(ibmx(1));
% state-update & tracking loop

*FIG. 15.1*

```
for ix = 1:Lx
    fQpUp = ix >= iqpSt; % detect bands with qp update
    if any(fQpUp)
        % update qp counter(s)
        nqpSt(fQpUp) = min (nqpSt (fQpUp)+1, NqpSt (fQpUp));

% update states
        nbQpUp = find(fQpUp);
        Nup = length(nbQpUp);
        for iup = 1:Nup
            ib = nbQpUp(iup);                              % band to update
            aqpmSt(ib) = sObj(ib) .aqpm(nqpSt(ib));        % update aqp state
            aqpSt(ib) = sObj(ib) .aqp(nqpSt(ib));          % Update aqp state
            iqpSt(ib) = sObj(ib) .iqp(nqpSt(ib));          % update iqp state
```

*FIG. 15.1 (Cont.)*

```
            LqpSt(ib) = sObj(ib).Lqp(nqpSt(ib));   % update Lqp state
        end % update tracking: guard band center
        [ammxi, immxi] = max(aqpmSt);
        if fQpUp(immxi) || immxi ~= immx(nqpm)
            % max band is a band that updated OR max @ new band
            nqpm = nqpm + 1;
            ammx(nqpm) = ammxi;
            immx(nqpm) = immxi;
            imqp(nqpm) = ix;
        end
```

```
% update tracking: main
iL = max(1, immxi - Ngrd);
iH = min(Nb, immxi + Ngrd);
ibnd = iL : iH;                         % GB range
[abmxi, nbmx] = max(aqpSt (ibnd));      % raw max-amp within GB
ibmxi = ibnd(nbmx);
if fQpUp(ibmxi) | | ibmxi ~= ibmx(nqp)

% max band is a band that updated OR max @ new band
        nqp = nqp + 1;
        abmx (nqp) = abmxi;
        ibmx (nqp) = ibmxi;
        nqmx (nqp) = nqpSt (ibmxi);
        Lbmx (nqp) = LqpSt (ibmxi);
        ixqp (nqp) = ix;
    end
  end
end sQpCmp.aqp = abmx (1:nqp);
sQpCmp.ibqp = ibmx (1:nqp);
sQpCmp.nqp = nqmx (1:nqp);
sQpCmp.Lqp = Lbmx (1:nqp);
sQpCmp.iqp = ixqp (1:nqp);
%
if nargout > 1
    sQpCmpm.aqp = ammx (1:nqpm);
    sQpCmpm.ibqp = immx (1:nqpm);
    sQpCmp.iqp = imqp (1:nqpm);
end return
```

← 3901 return
function sQpc = cleanQp (sQp)

% collect repeated-label patterns
dLqp = diff(sQp.Lqp);
if any (dlqp == 0)
    sQpc = colRepPatt(sQp);
end % reversal-by-1 pattern
dLqp = diff(sQpc.Lqp);
fRev1 = dLqp == -1 | dLqp == 3;
% action: remove
sQpc.aqp = sQpc.aqp(~fRev1);
sQpc.ibqp = sQpc.ibqp(~fRev1);
sQpc.Lqp = sQpc.Lqp(~fRev1);
sQpc.iqp = sQpc.iqp(~fRev1);

% collect remaining repeated-label patterns
dLqp = diff(sQpc.Lqp);
if any(dLqp == 0)
    sQpc = colRepPatt (sQpc);
end return

```
function sO = colRepPatt (sI)

% collect patterns of repeating-label qp's into single qp sO = sI;
nqpo = 0;
Nqp = length(sI.iqp);
fRep = false;
for nqp = 2:Nqp
        nqp1 = nqp-1;
      if ~fRep
         if sI.Lqp (nqp) == sI.Lqp (nqp1)
            % onset triggered: flag and wait for offset
            fRep = true;
            nqpOn = nqp1;
         else.
            % normal conditions: update
            nqpo = nqpo + 1;
            sO.aqp (nqpo) = sI.aqp (nqp1);
            sO.ibqp (nqpo) = sI.ibqp (nqp1);
            sO.iqp (nqpo) = sI.iqp (nqp1);
            sO.Lqp (nqpo) = sI.Lqp (nqp1);
            if nqp == Nqp
               % normal conditions @ last point: update again
               nqpo = nqpo + 1;
               sO.aqp (nqpo) = sI.aqp (nqp);
               sO.ibqp (nqpo) = sI.ibqp (nqp);
               sO.iqp (nqpo) = sI.iqp (nqp);
               sO.Lqp (nqpo) = sI. Lqp (nqp);
            end
      end
   end
end
```

*FIG. 17.2*

```
    if fRep && (sl.Lqp(nqp) ~= sl.Lqp (nqp-1) || nqp == Nqp)
        % offset triggered: collapse repeats to single qp
        fRep = false;
        if nqp ~= Nqp
            nqpOf = nqp1;
        else
            nqpOf = nqp;
    end
        nqpRng = nqpOn : nqpOf;
        % form mean of qp parameters (weighted by qp amplitude)
        nqpo = nqpo + 1;
        aqp = sl.aqp (nqpRng);
        saqp = sum (aqp);
        sO.aqp (nqpo) = saqp/length(aqp);   % mean qp amplitude
        sO.ibqp (nqpo) = sum (aqp.*sl.ibqp (nqpRng)) / saqp;
        sO.iqp (nqpo) = sum (aqp.*sl.iqp (nqpRng)) / saqp;
        sO.Lqp (nqpo) = sl.Lqp (nqpOn);
    end
end
sO.aqp = sO.aqp (1:nqpo);
sO.ibqp = sO.ibqp (1:nqpo);
SO.iqp = sO.iqp (1:nqpo);
sO.Lqp = sO.Lqp (1:nqpo);

return
```

METHOD AND SYSTEM FOR SIGNAL DECOMPOSITION, ANALYSIS AND RECONSTRUCTION

CROSS-REFERENCE TO RELATED APPLICATIONS

This application is a continuation of U.S. patent application Ser. No. 15/132,914, filed Apr. 19, 2016 (which issued as U.S. Pat. No. 9,734,838 on Aug. 15, 2017), titled "SYSTEM AND METHOD FOR SIGNAL DECOMPOSITION, ANALYSIS AND RECONSTRUCTION," which is a divisional of U.S. patent application Ser. No. 14/217,317, filed Mar. 17, 2014 (which issued as U.S. Pat. No. 9,319,028 on Apr. 19, 2016), titled "SIGNAL DECOMPOSITION, ANALYSIS AND RECONSTRUCTION USING HIGH-RESOLUTION FILTER BANKS AND COMPONENT TRACKING," which claims priority benefit, under 35 U.S.C. § 119(e), of U.S. Provisional Patent Application No. 61/801,292, filed Mar. 15, 2013, each of which is incorporated herein by reference in its entirety.

This application is related to

U.S. patent application Ser. No. 14/217,234, filed on Mar. 17, 2014, titled "METHOD AND APPARATUS FOR SIGNAL DECOMPOSITION, ANALYSIS, RECONSTRUCTION AND TRACKING (which issued as U.S. Pat. No. 9,530,425 on Dec. 27, 2016), as well as to U.S. patent application Ser. No. 13/220,679, filed Aug. 29, 2011 (which issued as U.S. Pat. No. 8,386,244 on Feb. 26, 2013), titled "SIGNAL DECOMPOSITION, ANALYSIS AND RECONSTRUCTION," which is a divisional of U.S. patent application Ser. No. 12/760,554, filed Apr. 15, 2010 (which issued as U.S. Pat. No. 8,010,347 on Aug. 30, 2011), titled "SIGNAL DECOMPOSITION, ANALYSIS AND RECONSTRUCTION APPARATUS AND METHOD," which is a divisional of U.S. patent application Ser. No. 11/360,135, filed Feb. 23, 2006 (which issued as U.S. Pat. No. 7,702,502 on Apr. 20, 2010), titled "APPARATUS FOR SIGNAL DECOMPOSITION, ANALYSIS AND RECONSTRUCTION," which claimed benefit of U.S. Provisional Patent Application 60/656,630, filed Feb. 23, 2005, titled "SYSTEM AND METHOD FOR SIGNAL DECOMPOSITION, ANALYSIS AND RECONSTRUCTION," each of which is incorporated herein by reference in its entirety. This application is also related to U.S. patent application Ser. No. 11/360,223, filed Feb. 23, 2006 (which issued as U.S. Pat. No. 7,706,992 on Apr. 27, 2010), titled "SYSTEM AND METHOD FOR SIGNAL DECOMPOSITION, ANALYSIS AND RECONSTRUCTION," which is incorporated herein by reference in its entirety.

FIELD OF THE INVENTION

This invention relates to the field of computer-implemented systems and methods, and more specifically a software-, embedded-circuits- or firmware-implemented system and method to decompose signals having quasi-periodic wave properties using high-resolution filter banks, to derive which filter band(s) contains the base signal of interest, to store such signals in a data structure, analyze such signals, and reconstruct such signals from the data structure, and/or to transmit such data structure over a communications channel.

COPYRIGHT & TRADEMARK NOTICES

A portion of the disclosure of this patent document contains material, which is subject to copyright protection. The owner has no objection to the facsimile reproduction by anyone of the patent document or the patent disclosure, as it appears in the Patent and Trademark Office patent file or records, but otherwise reserves all copyrights whatsoever.

Certain marks referenced herein may be common-law or registered trademarks of third parties affiliated or unaffiliated with the applicant or the assignee. Use of these marks is for providing an enabling disclosure by way of example and shall not be construed to limit the scope of the claimed subject matter to material associated with such marks.

FIGS. 10, 11.1, 11.2, 11.3, 12, 13, 14, 15.1, 15.2, 15.1 and 15.2 include source-code files that make up one embodiment of the present invention. These copyrighted source-code files are incorporated by reference in their entirety into this application. The owner has no objection to the facsimile reproduction by anyone of the patent document or the patent disclosure, as it appears in the Patent and Trademark Office patent file or records, but otherwise reserves all copyrights whatsoever.

BACKGROUND OF THE INVENTION

The digital representation of waveforms is a technology that is central to various sectors of industry where the detection of periodic and non-periodic waveforms can be critical to determining whether an erratic heartbeat, electrical short circuit, or some other problem exists. A digital representation must clearly and accurately represent the analog source of a waveform, but at the same time be able to accomplish such things as, compressing the incoming data into some manageable size, and maintain the integrity of the incoming data (i.e., making sure that the digital representation has enough fidelity to the original signal to be useful). Of additional import is the ability to have a digital representation that can consistently allow one to identify the presence and location of certain wave features, and/or that lends itself to certain types of automated analyses.

High-fidelity digital representations are problematic for a number of reasons. First, they require relatively large amounts of space within which to store the digitized data. Put another way, the higher the fidelity of the digitized data, the larger the amount of storage needed. Another problem with high-fidelity digital representations is that they can result in large amounts of digital data that has little or no import in terms of conveying meaning. For example, a periodic wave signal that merely repeats the same waveform does not convey much meaning to the person analyzing the waveform, and may in fact just take up storage space with unremarkable data. An additional problem is the repeated sampling, over sampling of such high-fidelity data even though it is otherwise unremarkable. Such over sampling results in wasted processing bandwidth (i.e., processor cycles, and/or power) as well as data bandwidth (data storage space and/or transmission bandwidth).

U.S. Pat. No. 6,785,700 issued on Aug. 31, 2004 with the title "Implementation of wavelet functions in hardware," and is incorporated herein by reference in its entirety. U.S. Pat. No. 6,785,700 describes an architecture component for use in performing a wavelet transform of a sampled signal, and an architecture including such components. The architecture component includes a multiplier, and a multiplexor to multiplex a number n of filter coefficients onto the multiplier. The multiplier processes n consecutive samples with consecutive coefficients, successive multiplier outputs being stored for subsequent processing to generate an output of the filter after every n samples. The wavelet transform may be a discrete wavelet transform or a wavelet packet decomposition. The architecture component may be configured to multiplex two or more coefficients onto a multiplier. Embodiments are disclosed in which the components are derived from a parameterized description in a hardware-description language.

U.S. Pat. No. 6,976,046 issued on Dec. 13, 2005 with the title "Architectures for discrete wavelet transforms," and is incorporated herein by reference in its entirety. U.S. Pat. No. 6,976,046 describes a microprocessor structure for performing a discrete wavelet transform operation, the discrete wavelet transform operation including decomposition of an input signal including a vector of $r^x k^m$ input samples, r, k and m being non-zero positive integers, over a specified number of decomposition levels j, where j is an integer in the range 1 to J, starting from a first decomposition level and progressing to a final decomposition level. The microprocessor structure has a number of processing stages, each of the number of processing stages corresponding to a decomposition level j of the discrete wavelet transform operation and being implemented by a number of basic processing elements, the number of basic processing elements implemented in each of the processing stages decreasing by a factor of k from a decomposition level j to a decomposition level j+1.

U.S. Pat. No. 7,346,640 issued on Mar. 18, 2008 with the title "Image processing apparatus supporting both discrete cosine transform and discrete wavelet transform," and is incorporated herein by reference in its entirety. U.S. Pat. No. 7,346,640 describes an image-processing apparatus supporting both discrete wavelet transform and discrete cosine transform with reduced hardware resources. The image-processing apparatus is composed of an input unit receiving a plurality of pixel data, a controlling unit selecting a desired transform from among discrete wavelet transform and discrete cosine transform, and providing a plurality of coefficients depending on the desired transform, and a processing unit which processes the pixel data using the plurality of coefficients to achieve the desired transform.

U.S. Pat. No. 7,480,416 issued on Jan. 20, 2009 with the title "Implementation of discrete wavelet transform using lifting steps," and is incorporated herein by reference in its entirety. U.S. Pat. No. 7,480,416 describes compact and efficient hardware architectures for implementing lifting-based DWTs, including 1-D and 2-D versions of recursive and dual scan architectures. The 1-D recursive architecture exploits interdependencies among the wavelet coefficients by interleaving, on alternate clock cycles using the same datapath hardware, the calculation of higher order coefficients along with that of the first-stage coefficients. The resulting hardware utilization exceeds 90% in the typical case of a 5-stage 1-D DWT operating on 1024 samples. The 1-D dual scan architecture achieves 100% datapath hardware utilization by processing two independent data streams together using shared functional blocks. The 2-D recursive architecture is roughly 25% faster than conventional implementations, and it requires a buffer that stores only a few rows of the data array instead of a fixed fraction (typically 25% or more) of the entire array. The 2-D dual-scan architecture processes the column and row transforms simultaneously, and the memory buffer size is comparable to existing architectures. The recursive and dual scan architectures can be readily extended to the N-D case.

U.S. Pat. No. 8,086,304 issued on Dec. 27, 2011, with the title "Physiologic signal processing to determine a cardiac condition," and is incorporated herein by reference in its entirety. U.S. Pat. No. 8,086,304 describes, that in a method for determining a cardiac condition, a sensed physiologic signal for a period of time including multiple cardiac cycles is received. Using the received physiologic data, a heart beat frequency to be used as a reference frequency is determined. A plurality of harmonics of the received physiologic signal is extracted based on the reference frequency, wherein the harmonics correspond to a plurality of alternans frequencies. Amplitudes of at least some of the extracted harmonics are determined, and are used to determine an alternans indicator value.

U.S. Pat. No. 8,498,177 issued Jul. 30, 2013 with the title "Determining a position of a geological layer relative to a wavelet response in seismic data," and is incorporated herein by reference in its entirety. U.S. Pat. No. 8,498,177 describes determining a position of a geological layer location in a subterranean formation, by receiving seismic data representing an interaction of the geological layer with propagation of a seismic wave, identifying a source wavelet representing a portion of the seismic wave impinging on a boundary of the geological layer, providing a geological layer template of the geological layer including primary and secondary reflection interfaces associated with reflectivity based on material properties of the geological layer, generating a wavelet response template by applying the source wavelet to the geological layer template using a mathematical convolution operation to model seismic wave interference caused by the primary and secondary reflection interfaces, identifying an extremum of the seismic data, and determining, based on the extremum, the location of the geological layer in the subterranean formation using the wavelet response template.

U.S. Pat. No. 8,595,278 issued on Nov. 26, 2013 with the title "Method and system for unconstrained frequency domain adaptive filtering," and is incorporated herein by reference in its entirety. U.S. Pat. No. 8,595,278 describes aspects of a method and system for unconstrained frequency domain adaptive filtering, including one or more circuits that are operable to select one or more time-domain coefficients in a current filter partition. A value may be computed for each of the selected one or more time-domain coefficients based on a corresponding plurality of frequency domain coefficients. The corresponding plurality of frequency-domain coefficients may be adjusted based on the computed values. A subsequent plurality of frequency-domain coefficients in a subsequent filter partition may be adjusted based on the computed values. Input signals may be processed in the current filter partition based on the adjusted corresponding plurality of frequency-domain coefficients. A time-adjusted version of the input signals may be processed in a subsequent filter partition based on the adjusted subsequent plurality of frequency-domain coefficients.

What is needed is a method and structure that efficiently and accurately captures the underlying waveform, with little or no degradation of the value and meaning of that waveform data. In particular, what is needed is a method and apparatus that tracks and records the properties of a particular frequency component of a complex waveform.

BRIEF SUMMARY OF THE INVENTION

In some embodiments, the present invention provides a method and apparatus that tracks and records the properties of a particular frequency component, such as the component corresponding to the time-local fundamental period of a quasi-periodic waveform (e.g., the rate and amplitude of the frequency component corresponding to, for example, the local cardiac cycle length of an electrocardiogram (ECG) signal, or a seismic signal) as that frequency component varies in frequency over a wide range of frequencies. Some embodiments provide a method and apparatus that perform digital filtering using a plurality of banks of filters whose frequency ranges overlap and whose center frequencies are closely spaced, and performing wavelet transforms on frequency components detected in the filtered signals from the plurality of banks of filters, and then tracking the components with the strongest signal within one of the overlapping filter banks (such that a particular frequency component that changes frequency over time can be tracked as its frequency shifts to higher or lower frequencies), in order to track that component as its frequency or period changes over a large range. In some embodiments, changes in frequency of up to 2:1 or 3:1 or more can be tracked. For example, a human heartbeat can often vary from fifty beats per minute (50 BPM, or even as low as 30 BPM or less) to two-hundred beats per minute (200 BPM or even 300 BPM or more). In some embodiments, the present invention tracks each of a plurality of frequency components of such a varying heartbeat, wherein each of the components shifts in frequency as the BPM rate changes.

In some embodiments, the present invention includes a system and method for representing quasi-periodic waveforms. For example, in some embodiments, the method includes representing each of a plurality of limited decompositions as a quasi-periodic waveform. Each quarter-phase ("QP") decomposition includes a first and second amplitude value and at least one time value. In some embodiments, each of the decompositions is phase adjusted such that the arithmetic sum of the plurality of limited decompositions reconstructs the quasi-periodic waveform. Data-structure attributes are created and used to reconstruct the quasi-periodic waveform. Features of the quasi-periodic wave are tracked using pattern-recognition techniques. The fundamental rate of the signal (e.g., heartbeat) can vary widely, for example by a factor of 2-3 or more from the lowest to highest frequency. To get quarter-phase representations of a component (e.g., lowest frequency "rate" component) that varies over time (by a factor of two to three) many bandpass filters are arranged with closely-spaced center frequencies to provide tracking of the component's frequency variation on a per-quarter-phase basis. Some embodiments provide tracking of the component's frequency variation on a per-digital-sample basis.

Accordingly, one aspect of the present invention provides a method and apparatus that tracks and records a particular frequency component (e.g., the rate and amplitude of the lowest (i.e., fundamental) frequency of, for example, the cardiac cycle of an electrocardiogram (ECG) signal) as that frequency component changes frequency over a wide range of frequencies.

In some embodiments, the present invention provides a method and apparatus that tracks and records a particular frequency component of, for example, a seismic signal, and analyzes the result to help predict earthquakes. In other embodiments, the present invention provides a method and apparatus that tracks and records a particular frequency component of, for example, certain types of internet messages, and analyzes the result to help predict human activity (e.g., commercial or social trends, or terrorism).

BRIEF DESCRIPTION OF THE DRAWINGS

FIG. 1.1 is a block diagram of a parallel filter bank system 100, according to some embodiments of the present invention.

FIG. 1.2 is a block diagram of a system 2300 of an input/analysis process 2301, an interpretive process 2305, a storage/transmission block 2309, and a re-synthesis/output process 2310, according to some embodiments of the present invention.

FIG. 2 is a block diagram of a subsystem 2400 used to track one component over a wide range of frequencies by an adaptive selection of a selected frequency band from among a bank of overlapping frequency bands within the signal decomposition function 2302 and the fractional-phase representation function 2303, according to some embodiments of the present invention.

FIG. 3.1 is a graph of the wavelet amplitude responses versus frequency of three wide-band wavelet bands, according to some embodiments of the present invention.

FIG. 3.2 is a graph of the wavelet amplitude responses versus frequency of three narrow-band wavelet bands, according to some embodiments of the present invention.

FIG. 3.3 is a graph 2503 illustrating a curve fit to three points, each representing an amplitude as the Y value and a frequency (or frequency index) as the X value, according to some embodiments of the invention.

FIG. 8 is a table 3000 of a number of beats-per-minute heart rates, the associated center frequency for each and the $k_r$ scaling parameter for each, according to some embodiments of the present invention.

FIG. 10 is a MATLAB program 3200 used to perform the QP transformation and obtain QP objects, according to some embodiments of the present invention.

FIGS. 11.1, 11.2 and 11.3 show three portions of a MATLAB program 3300 used to perform the QP transformation and obtain time-interpolated QP objects, according to some embodiments of the present invention.

FIG. 12 is a MATLAB program 3400 used to collect QP objects into a stream, according to some embodiments of the present invention.

FIG. 13 is a MATLAB program 3500 used to track a component of a signal, according to some embodiments of the present invention.

FIG. 14 is a MATLAB program 3600 used to smooth a stream of QP amplitudes, according to some embodiments of the present invention.

FIGS. 15.1 and 15.2 show two portions of a MATLAB program 3700 used to track a component of a signal based upon a reference center band and guard band, according to some embodiments of the present invention.

FIGS. 17.1 and 17.2 show two portions of a MATLAB program 3900 used to perform correction of QP label sequences with disturbances, according to some embodiments of the present invention.

DETAILED DESCRIPTION OF THE INVENTION

Figure 4:
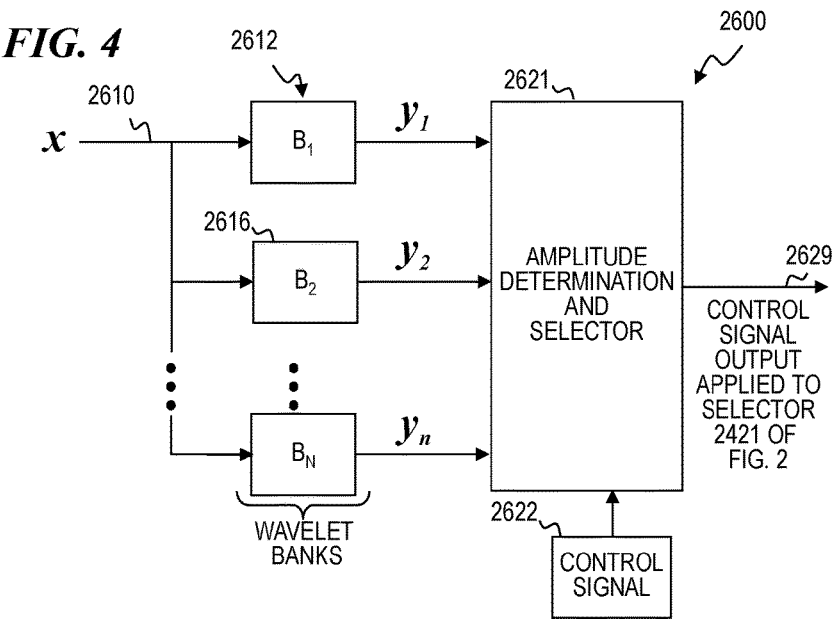
FIG. 4 is a block diagram of a subsystem 2600 used to generate a selection signal used to select one component over a wide range of frequencies, according to some embodiments of the present invention.

Although the following detailed description contains many specifics for the purpose of illustration, a person of ordinary skill in the art will appreciate that many variations and alterations to the following details are within the scope of the invention. Specific examples are used to illustrate particular embodiments; however, the invention described in the claims is not intended to be limited to only these examples, but rather includes the full scope of the attached claims. Accordingly, the following preferred embodiments of the invention are set forth without any loss of generality to, and without imposing limitations upon the claimed invention. Further, in the following detailed description of the preferred embodiments, reference is made to the accompanying drawings that form a part hereof, and in which are shown by way of illustration specific embodiments in which the invention may be practiced. It is understood that other embodiments may be utilized and structural changes may be made without departing from the scope of the present invention. The embodiments shown in the Figures and described here may include features that are not included in all specific embodiments. A particular embodiment may include only a subset of all of the features described, or a particular embodiment may include all of the features described.

Regarding the reference numbers appearing in the Figures—the same reference number is used throughout when referring to an identical component which appears in multiple Figures. Signals and connections may be referred to by the same reference number or label, and the actual meaning will be clear from its use in the context of the description.

For a detailed background description of some embodiments of the invention, see the handwritten notebook pages of U.S. Provisional Patent Application No. 61/801,292, filed Mar. 15, 2013, and Appendix A and Appendix B of U.S. Provisional Patent Application 60/656,630, filed Feb. 23, 2005, each of which is incorporated herein by reference in its entirety.

In some embodiments, a bandpass filter bank may be implemented using the Short-Time Fourier Transform (STFT), of which digital forms are well established utilizing the Fast Fourier Transform (FFT) at the website (referenced Mar. 13, 2014) en.wikipedia.org/wiki/Short-time_Fourier_transform.

In some embodiments, more control of the placement of center frequencies for the bands is obtained by using the "Chirp-Z Transform" (CZT) in place of the FFT in forming the STFT. The design criterion for the STFT is the choice of window function w(n), which in turn controls the bandwidth and stopband response of the resulting bandpass filters. These design choices are well understood in the art, and the considerations translate directly to those set forth in this specification and in the patents incorporated herein by reference.

In some embodiments, the impulse response of a digital bandpass may be expressed as $h(n)=w(n)*\exp(-j2\pi f_c nT)$ where $\exp(x)=e^x$, $j=\sqrt{-1}$ (square root of minus one), $f_c$ is the center frequency in Hz, n is a time-sampling index, and T is the sampling period of the data in seconds. This is a modulated-window form, where w(n) defines a prototype low-pass filter function, and the complex exponential modulates (shifts the frequency response of) the low-pass up so that it is centered not at 0 Hz but at fc.

In practice, a bandpass-filtered output signal y(n) is formed through a process of convolution between impulse response h(n) and input signal x(n), through a convolution sum: $y(n)=\Sigma_m h(m)\times(n-m)=\Sigma_m x(m) h(n-m)$ (i.e., y(n)=sum_over_m(h(m)*x(n-m))=sum_over_m(x(m)*h(n-m))).

For h(n) of finite length, the summation is of finite length for each computed output point at sample index n. Substituting the above-defined h(n) to the above convolution yields a form of the STFT. In some embodiments, the convolution process is performed using frequency-domain techniques to increase computational efficiency, using, for example, methods such as the "overlap-add" or "overlap-save" methods.

In some embodiments, specification of w(n) for both the STFT and the above-defined digital bandpass filter controls the bandwidth and general response behavior of the filter, design considerations for which are known extensively in the art of digital low-pass filter design, as may be found at website en.wikipedia.org/wiki/Digital_filter, and in the following references:

S. K. Mitra, Digital Signal Processing: A Computer-Based Approach, New York, N.Y.: McGraw-Hill, 1998.

A. V. Oppenheim and R. W. Schafer, Discrete-Time Signal Processing, Upper Saddle River, N.J.: Prentice-Hall, 2010. (In Oppenheim & Shafer, Chapters 6 & 7 cover filter design in detail.)

In some embodiments, the digital bandpass may be implemented based upon wavelets as found in the following reference: The Illustrated Wavelet Transform Handbook, Paul S. Addison, Institute of Physics Publishing, 2002; particularly as in Chapter 2, per the Morlet Wavelet. While the Morlet Wavelet is formally defined for continuous-time, it may be expressed in sampled-time form by substituting time variable t with nT, where n is the time-sampling index and T is the sampling interval expressed, e.g., in seconds. As such, the Morlet Wavelet is a special case of the modulated-window form of the digital bandpass filter above, where w(n) is Gaussian in shape.

As used herein, a wavelet-transform function is sometimes referred to as a wavelet or wavelet transfer function and each has the same meaning as the other(s); two or more wavelet-transform functions are sometimes referred to as wavelets, and each has the same meaning as the other(s); a digitized signal is sometimes referred to as signal X, and each has the same meaning as the other; a particular frequency component of a decomposed signal X are sometimes referred to as a component, and each has the same meaning as the other; bandpass wavelet-transform functions are sometimes referred to as bandpass wavelets or as bandpasses, and each has the same meaning as the other(s); a problem is sometimes referred to as an issue and each has the same meaning as the other; and the term "without loss of generality" is sometimes abbreviated w.l.o.g.—and is intended to mean that the preceding discussion is just one example—thus in other embodiments of the invention, other suitable parameters are used.

In some embodiments, the first data structure further includes linked attributes, including: a descriptor that includes a difference of abscissa values between the abscissa value included in the particular data structure and the abscissa value included in a first linked data structure relative to this particular data structure, a descriptor that includes a difference of abscissa values between the abscissa value included in the particular data structure and the abscissa value included in a second linked data structure relative to this particular data structure, a descriptor that includes an indication of deviation from an expected sequence of phase labels, and a descriptor that includes a moving average of abscissa values for a group of data structures surrounding the particular data structure.

FIG. 1.1 is a block diagram of a parallel filter bank 100, in general implemented as more fully described in U.S. Pat. No. 7,702,502 that issued on Apr. 20, 2010 with the title "APPARATUS FOR SIGNAL DECOMPOSITION, ANALYSIS AND RECONSTRUCTION", which is incorporated herein by reference in its entirety. U.S. Pat. No. 7,702,502 describes a method of signal decomposition using filter bank 100 having a parallel arrangement of N filter sections that use the Parallel-Form Kovtun-Ricci Wavelet Transform. In some embodiments, parallel filter bank 100 is implemented in software, firmware, hardware, and/or combinations thereof. An original signal x 101 is applied to the input of the bank, and a set of N component signals $y_1 \ldots y_N$ 104 are provided at the outputs of the N filter sections (also called "component bands", "band filters" or simply, "bands") of filter bank 100. In some embodiments, the filter sections each include a cascade of a component filter H and a delay element D, with the component filters having transfer functions denoted by $H_1 \ldots H_N$ 102, and the delay elements having transfer functions denoted by $D_1 \ldots D_N$ 103. The $p^{th}$ filter section 105 of filter bank 100, where p is an integer between 1 and N, inclusive, is thus comprised of component filter $H_p$ 106 (one example of which is discussed further in the below-described FIG. 2) and delay element $D_p$ 107. Original input signal x 101 is provided at the inputs of all filter sections of filter bank 100, each of which produces corresponding stream of values of the component signal $y_p$ 108, where p is an integer between 1 and N, inclusive.

In some embodiments, a fractional-phase determination function generates a fractional-phase representation of each component signal $y_p$ 108. For example, in some embodiments, the fraction is ¼ and the functions are quarter-phase parameter-determination functions $QP_1$-$QP_N$ 110 that determine four time values (one time value for each "quarter" phase (first zero-crossing to amplitude maximum, amplitude maximum to second zero-crossing, second zero-crossing to amplitude minimum, and amplitude minimum to final zero crossing of a single cycle)) and two amplitude values (amplitude maximum and amplitude minimum) to generate each quarter-phase representation objects $QP_1$-$QP_N$ 109; however, other embodiments can use other fractions. In the embodiment shown, a plurality of streams of quarter-phase representation objects $QP_1$-$QP_N$ 109 is output, wherein each stream is a sequential series of successive quarter-phase representation objects $QP_P$, each based upon the corresponding component signal $y_p$ 108. Each component signal $y_p$ 108 and each set of quarter-phase-representation objects $QP_P$ are associated (in some embodiments, implicitly) with the center frequency of their corresponding band filter $H_P$-$D_P$. In some embodiments, the center frequency of each filter band is fixed, so it can be difficult to accurately track a signal (such as a heart beat) that has a wide range of possible frequencies, and whose rate can change rapidly.

In some embodiments, the present invention as represented by FIG. 1.1 and FIG. 1.2 improves upon the invention of U.S. Pat. No. 7,702,502 by replacing at least one band filter-and-QP process (e.g., the $p^{th}$ filter-and-QP section 120) with a further parallel bank of filter-and-QP processes 2400 (see FIG. 2) whose associated band filters have a closer frequency spacing than the frequency spacing used by the band filters in parallel filter bank 100. In some embodiments, the $p^{th}$ filter-and-QP section 120 that is replaced or supplemented by bank 2400 is that section for the band designed for the lowest (or fundamental) frequency component of input signal x 101.

Thus, in contrast to the system described in U.S. Pat. No. 7,702,502, which used one single-band filter for each frequency component and/or fewer than two band center frequencies per octave, the present invention replaces at least one component's band filter and QP processing 120 of FIG. 1.1 (and the corresponding functions 2302 and 2303 described below) with a bank of band filters and associated QP processes (e.g., bank 2400 of FIG. 2 described below) and a selector that selects, from among the plurality of QP outputs, that QP output having the strongest signal. In some embodiments, the sequential series of successive quarter-phase representation objects $QP_P$ from that bank includes a frequency parameter (e.g., an index of the filter band from which the signal was obtained, or the actual frequency or rate, or some other value corresponding to at least one of these parameters) as well as the four time values and two amplitude values in the QP objects described in U.S. Pat. No. 7,702,502. In some embodiments, the QP objects of the present invention also include other parameters as described in U.S. Pat. No. 7,702,502.

FIG. 1.2 is a block diagram of a system 2300. As described more fully in U.S. Pat. No. 7,702,502 (which is incorporated herein by reference in its entirety), in some embodiments, system 2300 includes an input/analysis process 2301, an interpretive process 2305, a storage/transmission block 2309, and a re-synthesis/output process 2310. In some embodiments, the Input/Analysis Process block 2301 takes the original signal and produces a corresponding stream of objects (in some embodiments, this output includes a plurality of streams of QP objects including a stream of successive quarter-phase representation objects $QP_P$ with frequency parameter(s) from bank 2400 of FIG. 2). In some embodiments, the original signal is applied to the Signal Decomposition block 2302, the output of which is the set of corresponding component signals. These signals are then processed in the Fractional Phase Representation block 2303 to identify the object boundaries and measure basic attributes, and the corresponding object-related information is passed to the Object Construction and Linking block 2304 to construct the object streams, filling out whatever additional object-related, data structure related information (i.e., attributes, links, etc.) is needed in a particular application. In cases of multiple original signals, the Input/Analysis Process block would be repeated and/or duplicated for each original signal. The resulting object streams from each Process may then be merged into a single composite stream of objects.

The Interpretive Process block 2305 takes the object stream and produces an interpretation of the original signal(s). In some embodiments, the State Construction block 2306 takes the object stream and constructs states from them. The resulting series of states, along with the underlying objects by which they are defined, then form the input to the Organized Mapping block 2307, where the information is mapped in state space and/or a vector space along one or more object attributes. As stated in the context of this invention, the information may be mapped directly in some ad-hoc manner, for example using a sequence detector on the states and/or some nonlinear, neural and/or fuzzy map formed on the object attributes. In some embodiments, the information may also be used for training a model. Once trained, the information may be applied to the model to produce a mapped output. In some embodiments, the mapped information is then passed to a Pattern Recognition, Discrimination and/or Display block 2308 to transform the mapped information into a human-interpretable form, such as for example an automated identification and/or diagnosis of a certain condition, and/or visualization of relevant mapped information. Automated identification could involve simple thresholding on the mapped information, or could use more sophisticated detection and discrimination techniques such as Novelty Detection and Support Vector Machines. (See *The Nature of Statistical Learning Theory* $2^{nd}$ *Edition*, by V. Vapnik, Springer 1995; *Support-Vector Learning*, by C. Cortes and V. Vapnik, 20 Machine Learning 1995 (which are both incorporated herein by reference in their entirety)).

The Storage/Transmission block 2309 takes the object stream and/or the original signal samples and/or samples of the component signals (or a predetermined select subset of the component signals) and stores some or all of them in memory and/or transmits some or all of them over a communications link. The Re-synthesis/Output Process block 2310 takes the object stream from a communications link and/or storage and reconstructs an estimate of the original signal(s). The object stream corresponding to a desired original signal is recovered from storage and/or received from a communications link via the Retrieval/Reception block 2311. Estimates of the component signals for the desired original signal are then produced by the Component Reconstruction block 2312, and the component signal estimates are then combined in the Signal Reconstruction block 2313 to produce an estimate of the desired original signal. If desired, the individual component signals may be output from the Re-synthesis/Output Process block 2310 as well. Multiple original signals may be reconstructed using multiple instances of this Process, once for each desired original signal. The reconstructed signal(s) may then be displayed, for example, on a plot trace (or series of plot traces) for human interpretation, if desired, along with the output of the Interpretive Process block 2305.

Adaptive (Controlled) QP Parameters

FIG. 2 is a block diagram of a method and apparatus for processing QP parameters to obtain adaptive parameters useful for tracking varying frequency components, wherein x=digitized input signal 2401, $B_1, B_2, \ldots B_N$=Wavelet filters bank 2412, $QP_1, QP_2, \ldots QP_N$=a bank of quarter-phase generators 2410 corresponding to each frequency band 2406, $QP_1, QP_2, \ldots QP_N$=a set of streams of quarter-phase parameters 2409 corresponding to each frequency band.

In some embodiments, QP selector 2421 is controlled by a selection (control) signal 2422 and selects, at given point in time, one QP stream of the set of QP streams: $QP_1$, $QP_2 \ldots QP_N$.

In some embodiments, selection signal 2422 may indicate the band having the maximum power or amplitude from among the bands operating on signal x 2401, where a band having maximum amplitude means one of the bands having an amplitude no lower than the other bands in the associated bank. (For purposes of generating the selection or indication signal, the terms "maximum-power" and "maximum-amplitude" are to be used interchangeably.) In some embodiments, selection signal 2422 may indicate the band having the maximum power or amplitude from among the bands operating on another signal, or in another frequency range. In some embodiments, by associating the maximum-amplitude band indication with the band's center frequency, an estimate of the component frequency is formed, and used as a frequency estimate signal.

In some embodiments, selection signal 2422 indicates a plurality of the bands from which an interpolation can be made from amplitudes of bands surrounding the band having the maximum amplitude. In some embodiments (where two bands could possibly have the same maximum amplitude), the present invention selects one of the bands that has an amplitude no lower than the other bands in the bank (i.e., one of the banks having the maximum amplitude). In some embodiments, the center frequencies of the bands form the x-values of the points to be interpolated, and the associated band amplitudes form the y-values of the points to be interpolated, for example, through a curve fit or a spline. In some embodiments, the interpolation is in the form of a polynomial fit, with a fit of polynomial order N requiring at least N+1 point values (and thus at least N+1 bands including the maximum-amplitude band). In some embodiments, a second-order polynomial (parabolic) fit is performed, as the convex parabola has a single well-defined peak and a shape consistent with an amplitude peak. The parabolic fit would thus require at least three point values. Performing the parabolic fit and solving for the peak of the (convex) parabola results in an amplitude value and frequency value that estimate respectively the amplitude and frequency of the frequency component, with higher resolution than estimates formed from simple selection of the maximum-amplitude band.

See the illustrative discussion below of curve fitting for FIG. 3.3.

In some embodiments the x-values of the fit are formed from indices corresponding to the ordered position of the respective bands. Performing the parabolic fit and solving for the peak then results in an interpolated index. In some embodiments the interpolated index can be mapped to the band frequencies through a mapping function or interpolated table lookup to determine an associated frequency. In some embodiments the interpolated index may be used along with the QP values of the bands whose indices straddle the interpolated index, to form an interpolated QP value with a higher-resolution than either of the direct QP values from the bands.

In some embodiments, the band frequencies of the filters are spaced logarithmically, and the instantaneous frequency is determined by interpolating upon the logarithms of the band frequencies.

The present invention tracks the frequency of a component of a signal x(n), and is well-suited for signals with widely varying fundamental periodicities. Consider the case where the fundamental periodicities in quasi-periodic signal X (which is digitized to form the digitized input signal x 2401 of FIG. 2) varies over a substantially wide range, e.g., where the ratio of the highest frequency to the lowest of the periodicity is a factor of two or more. For signal x 2401 that is not locally sinusoidal, the local TFA (time-frequency analysis) will show energy at the fundamental frequency $f_0(t)$ and substantially integer harmonics $n \cdot f_0(t)$, where n is an integer, or in general $x = \Sigma_n a_n(t) \cdot \cos(\phi_n(t))$, where $a_n(t)$ is the amplitude function of time for the nth frequency component, and $\phi_n(t)$ is the corresponding phase function.

An example phase function would be $\phi_n(t)=\int q_n f(t)dt+\varphi_n(t)$, where the $q_n$ denote frequency factors from one component to the next. Typically $q_n$ is a monotonically increasing series, and the $\phi_n(t)$ are representative of the locally static phase relationship from one component to the next. The spacing of the $q_n$ for adjacent values of n denotes the (local) frequency spacing between components.

Note that for determining the fundamental period of a component, in some embodiments, it is preferable for the component output from the wavelet band to be locally sinusoidal, so that the QP sequence generation is "clean" (i.e., does not exhibit reversals in the sequence ABCD) and does not show significant interference from neighboring components of X.

In some embodiments having only one wavelet band per component, difficulty may arise in specifying/designing the frequency response of the band. The wavelets/bands should be sufficiently narrow-band to emphasize the (rate) component of interest and suppress other components. The wavelet bandwidth can be an issue if the component spacing is narrower than the expected rate range. In this case, for the wavelets to cover the frequency range of interest covered by the component, at some frequencies of the component (e.g., lower frequencies of the range), the next-higher component will be still passed by the wavelet transfer function (frequency response). (Likewise, at higher frequencies of the component range, the next-lower component could be passed by the wavelet.) Interfering neighboring components could then appear at the wavelet output, resulting in potentially substantial deviation from a locally sinusoidal wave shape at the wavelet output.

Of course, narrowing the wavelet bandwidth results in limited coverage of frequency range for the component, as the wavelet response significantly attenuates the component at the edges of the wavelet band, requiring that the component not vary widely in frequency. This creates difficulty in extracting and/or tracking certain desired frequency components of the initial digitized signal x if the desired component has a wide range of possible frequencies (or rates, expressed for example in cycles per second), particularly if the 0signal has multiple components spaced at frequency factors narrower than the ratio of the highest to lowest frequency in the frequency range of the desired component. The present invention provides a solution to this problem.

In some embodiments, the solution that allows resolving of the desired component from a component set over a substantially wide range of fundamental component frequencies consists of replacing a single-band process $H_n$ in a bank (e.g., $H_P$ 106 in bank 100 of FIG. 1.1) with a bank 2412 (See FIG. 2) of wavelets.

FIG. 3.1 is a graph 2501 of the frequency response (the amplitude response) of a wavelet band 2512 with two neighboring bands 2511 (the next-lower-frequency component band, having a cross-over point 2515 with band 2512) and 2513 (the next-higher-frequency-component band, having a cross-over point 2516 with band 2512).

In the present invention, each frequency-component band (e.g., 2511, 2512 and 2513) processes an initial digitized signal x through a digital bandpass filter configured to have a center frequency and a bandwidth, each of which is specified by a respective parameter. In some embodiments, each digital bandpass filter is implemented as a software routine and/or hardware circuit that can be executed in parallel or serially with other ones of the digital bandpass filters. In some embodiments, the digital bandpass filters are implemented using wavelets. In some embodiments, the outputs of the digital bandpass filters are each sequential streams of digital values denoted as $y_n$. In some embodiments, each stream $y_n$ of digital values is processed by a respective fractional-phase reduction unit (again, implemented as software routines and/or hardware circuits) that reduces the amount of data while retaining certain essential characteristics, and outputs a stream of digital values denoted as $FP_n$. In some embodiments, the fractional-phase reduction unit is implemented as a quarter-phase reduction unit, so each stream $y_n$ of digital values is processed by a respective quarter-phase unit (again, these are implemented as software routines and/or hardware circuits) that reduces the amount of data while retaining certain essential characteristics, and outputs a stream of digital values denoted as $QP_n$.

In some embodiments, this bank 2400 of FIG. 2 is designed with bandpass wavelets with center frequencies disposed such that their responses overlap substantially. In this case, the bands are not necessarily designed to decompose the signal X into components (although they could be used for that in other embodiments), but to identify where in frequency the desired component(s) have significant (dominant) energy (power). The bank of overlapping bandpasses operating on signal x will be excited by varying degrees in response to a time-local frequency component. The amplitudes of the wavelet outputs $y_n$ may thus be analyzed at each (or certain) points in time to determine the characteristics of x as a function of frequency (or with respect to frequency). In some embodiments, the amplitude of the wavelet output may be analyzed at each point in time and the largest (maximum) found across bands. In some embodiments, this then forms the basis for a control selection signal 2422 for selecting the desired component signal from among the wavelet outputs 2404 or from among set of streams of quarter-phase parameters 2409 as described in the description of FIG. 2.

In some embodiments, the bandpass ranges (passbands) of the bands of each of a plurality of particular bands in wavelet filter bank 2412, relative to that of its closest-neighboring band on either the higher- or lower-frequency side, are such that the cross-over point between one band and the next is only about −0.1 dB from the maximum response at the center frequencies of either of the two bands. In some embodiments, each band's filter's response at the cross-over point with the neighboring (next) band is no further than about −0.2 dB from the maximum response at the band's center frequency. In some embodiments, each band's filter's response at the cross-over point with the neighboring band is no further than about −0.5 dB from the maximum response at the band's center frequency. In some embodiments, each band's filter's response at the cross-over point with the neighboring band is no further than about −0.75 dB from the maximum response at the band's center frequency. In some embodiments, each band's filter's response at the cross-over point with the neighboring band is no further than about −1 dB from the maximum response at the band's center frequency. In some embodiments, each band's filter's response at the cross-over point with the neighboring band is at least about −1 dB from the maximum response at the band's center frequency.

FIG. 3.2 is a graph 2502 the frequency response (the amplitude response) of a wavelet band 2522 with two neighboring bands 2521 (the next-lower-frequency component band) and 2523 (the next-higher-frequency-component band). In some embodiments, the filter for each respective band (2521, 2522, 2523) has the same center frequency but a narrower bandwidth than the corresponding wider-band filters used to obtain each respective band (2511, 2512, 2513) in graph 2501 of FIG. 3.1. In some embodiments, the filter for each respective band (2521, 2522, 2523) has center frequencies spaced more narrowly than the spacing of the center frequencies of the wider-band filters used to obtain certain bands (2511, 2512, 2513) in graph 2501 of FIG. 3.1. In some embodiments, the bandpass ranges in of the bands of each of a plurality of particular bands used for deriving the selection signal 2422 to its closest-neighboring band on either the higher- or lower-frequency side are such that the cross-over point between one band and the next is no further than about −1 dB from the maximum response at the center frequencies of the two bands. In some embodiments, each band's filter's response at the cross-over point with the next band is no further than about −0.2 dB from the maximum response at the band's center frequency. In some embodiments, each band's filter's response at the cross-over point with the next band no further than about −0.5 dB from the maximum response at the band's center frequency. In some embodiments, each band's filter's response at the cross-over point with the next band is no further than about −0.75 dB from the maximum response at the band's center frequency. In some embodiments, each band's filter's response at the cross-over point with the next band is at least about −1 dB from the maximum response at the band's center frequency.

FIG. 3.3 is a graph 2503 illustrating a curve fit to three points, each representing an amplitude as the Y value and a frequency (or frequency index) as the X value, according to some embodiments of the invention. In some embodiments, the three (X,Y) points 2531, 2532, and 2533 represent the outputs of three bands of digital bandpass filters at some time point (or time point within a time period such as a given quarter phase). In this example, point 2532 is the maximum amplitude of a bank of bands (for example the band having the frequency response 2522 of FIG. 3.2 or the band having the frequency response 2512 of FIG. 3.1. Reference 2521.1 is the center frequency (or the index of the band) of a lower-frequency band in the neighborhood of the band of point 2532 (in some embodiments, the next-lower frequency band), reference 2522.1 is the center frequency (or the index of the band) of the band that output the maximum amplitude in the bank-associated with point 2532, and 2523.1 is the center frequency (or the index of the band) of a higher-frequency band in the neighborhood of the band of point 2532 (in some embodiments, the next-higher frequency band). In some embodiments, a curve fit operation (as described above) results in curve 2534 having a maximum amplitude 2535 at an interpolated peak frequency (or frequency index) 2536. In some embodiments, amplitude 2535 and frequency (or frequency index) 2536 represent a higher accuracy and/or higher precision estimate of both the amplitude and frequency of the tracked component than would result from selecting the amplitude and center frequency of point 2532, which is the maximum-amplitude band of the bank that is used for tracking the tracked component.

In some embodiments, the interpolated frequency result not only provides higher resolution than using the center frequency or integer index of the digital bandpass filter having the maximum response, but the interpolated frequency result also allows the present invention to use different center frequencies for the digital bandpass filters used to derive the selection signal 2422 as compared to the center frequencies for the digital bandpass filters used to derive the data 2409 being selected by selector 2421.

Thus, in some other embodiments of the present invention that do not use interpolation, the integer index (e.g., in some embodiments, the value r of FIG. 8) of the band having the maximum response (or the corresponding center frequency $f_A$ of FIG. 8—for example. index r=2 corresponds to a center frequency $f_A$=0.4887 Hz in FIG. 8) is used to select the band process 2420 from which to obtain the tracked frequency and amplitude of the tracked component.

In contrast, in some embodiments of the present invention using interpolated amplitude and frequency, the non-integer index (e.g., in some embodiments, the value of reference number 2536 of FIG. 3.3) derived from the band having the maximum response and a neighboring band on each side of that band (or the corresponding center frequencies $f_A$ of FIG. 8—for example. indexes r=1, 2, and 3 correspond to center frequencies $f_A$=0.4691, 0.4887 and 0.5044 Hz in FIG. 8) is used to select the bands (i.e., band 2420 and one or two neighboring bands of FIG. 2) from which to interpolate the tracked frequency and/or amplitude and/or other QP parameters (for example, a QP time point for corresponding QP labels) of the tracked component. Thus these embodiments can use different center frequencies for the digital bandpass filters used to derive the selection signal 2422 as compared to the digital bandpass filters used to derive the QP data 2409 being selected. For example, if center frequencies 2521.1, 2522.1 and 2523.1 of FIG. 3.3 (and/or FIG. 3.2) happened to be 0.45 Hz, 0.49 Hz and 0.52 Hz, and the resulting interpolated frequency 2536 result was 0.51375 Hz (for example), then that resulting interpolated frequency of 0.51375 Hz and/or the curve fit used to obtain it would be used to interpolate the amplitude for the tracked component from, say two or three bandpass filters having different center frequencies (for example if center frequencies 2511.1, 2512.1 and 2513.1 of FIG. 3.1 had center frequencies $f_A$=0.4887, 0.5044 Hz and 0.5271 (corresponding to indexes 2, 3, and 4 of FIG. 8)) using the interpolated frequency of 0.51375 Hz and/or the curve fit parameters. In some embodiments, quarter phases of the tracked component are obtained by interpolating between quarter-phase streams of two neighboring QP units from QP bank 2410 (see FIG. 2).

FIG. 4 is a block diagram of a subsystem 2600 used to generate a selection signal used to select one component over a wide range of frequencies, according to some embodiments of the present invention. In some embodiments, subsystem 2600 includes a plurality of bandpass wavelet bands 2612, each operating on signal x and producing one or more band outputs each being a sequence of filtered values $y_n$ (band signals) that are each analyzed by amplitude determination and selector 2621. In some embodiments, amplitude determination and selector 2621 determines the amplitude of each of the band signals $y_n$ and selects one of the band signals that is from the band having the maximum amplitude value as determined by amplitude determination and selector 2621 without a selection signal; in other embodiments, amplitude determination and selector 2621 selects one of the band signals $y_n$ that is from the band having some selected value as determined by amplitude determination and selector 2621 based on selection signal 2622. In some embodiments, amplitude determination and selector 2621 selects a plurality of the band signals $y_n$ that are from the bands having near to the maximum value as determined by amplitude determination and selector 2621 without a selection signal; in other embodiments, amplitude determination and selector 2621 selects a plurality of the band signals $y_n$ that are from those certain selected bands based on selection signal 2622. In some embodiments, the amplitude of each of the band signals $y_n$ is determined and then smoothed (e.g., using low-pass filters, moving averages, or the like) before it enters unit 2621.

Figure 5:
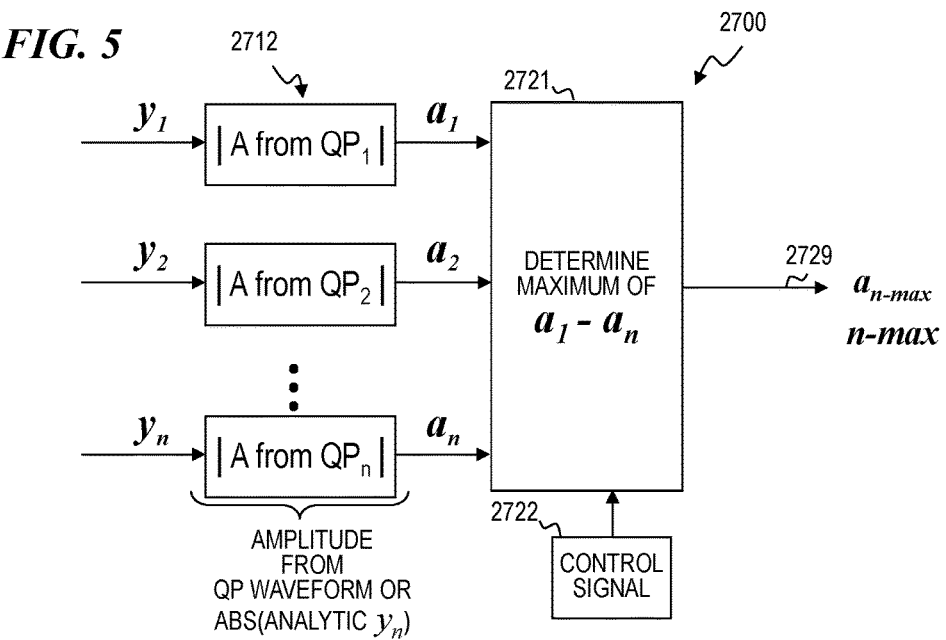
FIG. 5 is a block diagram of a subsystem 2700 used to generate a selection signal used to select one component over a wide range of frequencies, according to some embodiments of the present invention.

FIG. 5 is a block diagram of a subsystem 2700 used to generate a selection signal used to select one component over a wide range of frequencies, according to some embodiments of the present invention. In some embodiments, subsystem 2700 includes a plurality of quarter-phase amplitude-determination units 2712, each generating one or more streams of QP values each being a sequence of $QP_n$ objects including time values as well as quarter-phase amplitude values $a_n$ that are each analyzed by amplitude determination and selector 2721. In some embodiments, amplitude determination and selector 2721 selects one of the sequence of amplitude values $a_n$ that is from the band having the maximum value as determined by amplitude determination and selector 2721 without a selection signal; in other embodiments, amplitude determination and selector 2721 selects one of the sequences of amplitude values $a_n$ that is from the band having some selected value as determined by amplitude determination and selector 2721 based on selection signal 2722. In some embodiments, amplitude determination and selector 2721 selects a plurality of the filtered sequence of amplitude values $a_n$ that are from the bands having near to the maximum value as determined by amplitude determination and selector 2721 without a selection signal; in other embodiments, amplitude determination and selector 2721 selects a plurality of the plurality of sequences of amplitude values $a_n$ that are from those certain selected bands based on selection signal 2722. In some embodiments, each of the sequences of amplitude values $a_n$ is smoothed before it enters unit 2721 (e.g., using low-pass filters, moving averages, or the like).

Figure 6:
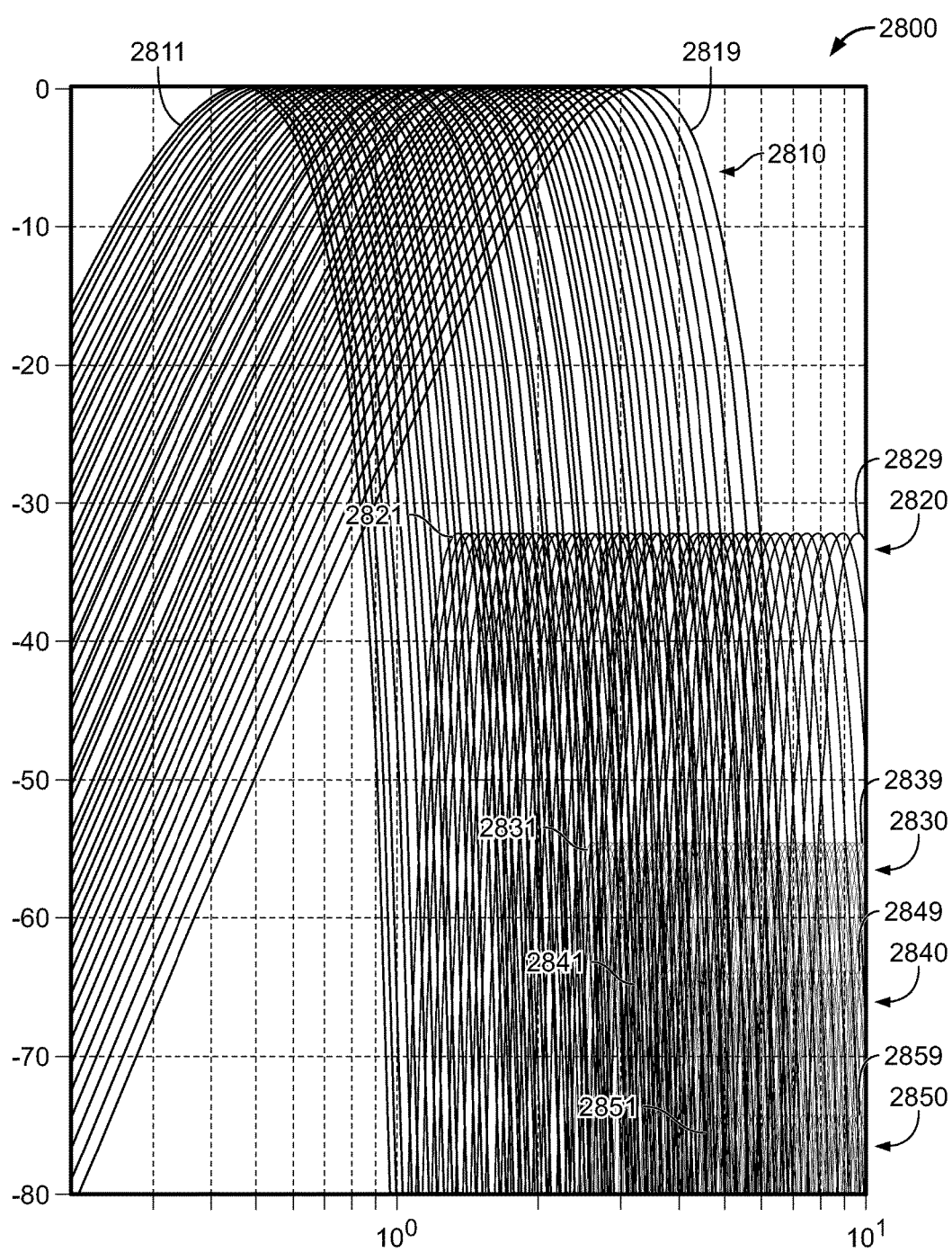
FIG. 6 is a graph 2800 of the wavelet amplitude responses versus frequency of about forty-seven wide-band wavelet bands, according to some embodiments of the present invention.

FIG. 6 is a graph 2800 of the wavelet amplitude responses versus frequency of a plurality of wide-band wavelet bands, according to some embodiments of the present invention. In some embodiments, the main responses 2810 include a plurality of bands having mainlobes 2811-2819, and each band has a plurality of sidelobes. In some embodiments, the first plurality of sidelobes 2820 have peaks about −32 dB from the mainlobe response peaks, and sidelobes 2821-2829 each correspond to a respective one of the mainlobes 2811-2819; the second plurality of sidelobes 2830 have peaks each about −54 dB from the main response peaks, and sidelobes 2831-2839 each correspond to a respective one of the mainlobes 2811-2819; the third plurality of sidelobes 2840 have peaks each about −64 dB from the main response peaks, and sidelobes 2841-2849 each correspond to a respective one of the mainlobes 2811-2819; the fourth plurality of sidelobes 2850 have peaks each about −74 dB from the main response peaks, and sidelobes 2851-2859 each correspond to a respective one of the mainlobes 2811-2819.

Figure 7:
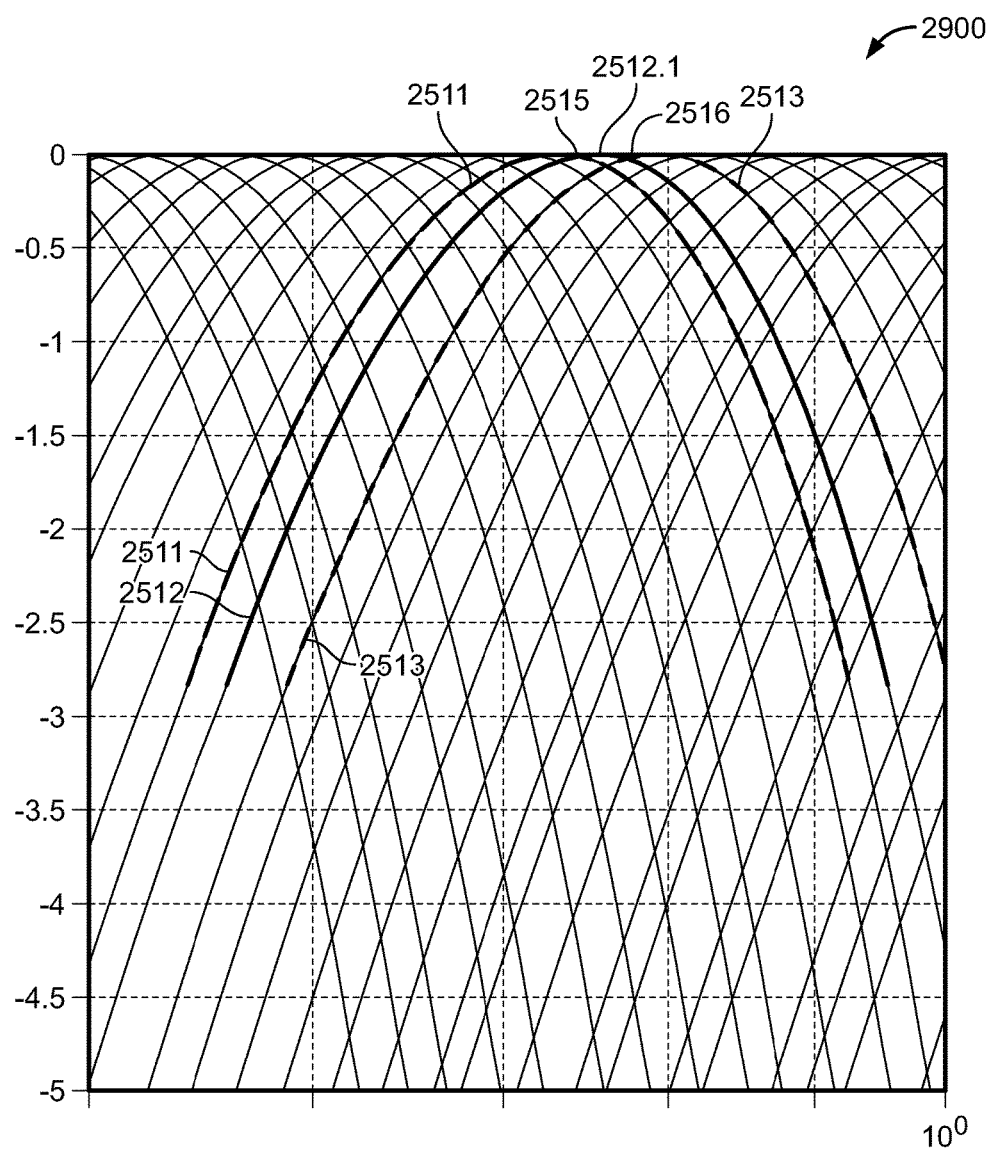
FIG. 7 is an enlarged portion 2900 of graph 2800 of the wavelet amplitude responses versus frequency of a large number of (in this case, about forty-seven) wide-band wavelet bands, according to some embodiments of the present invention.

FIG. 7 is an enlarged portion 2900 of graph 2800 of the bandpass wavelet amplitude responses versus frequency of a large number of wide-band bandpass wavelet bands, according to some embodiments of the present invention. In some such embodiments, one bandpass wavelet band 2512 (solid emphasis line) has two neighboring bands: the next-lower-frequency component band 2511 (long-dashed emphasis line), having a cross-over point 2515 with band 2512, and the next-higher-frequency-component band 2513 (short-dashed emphasis line), having a cross-over point 2516 with band 2512. In some such embodiments, the cross-over points are less than −0.1 dB from the maximum response magnitude.

Graph 2800 shows magnitude frequency response as example of wavelet bank for adaptive system of FIG. 2 or for control-signal generation of FIG. 4 and FIG. 5 described above. Some embodiments of the design use architecture described in the descriptions of FIGS. 3.1, 3.2, 4, 5, 6, 7, 10 and 11.1-11.3. This an analytic bank, with these responses corresponding to the real part (the response corresponding to the imaginary part are implied by extension). FIG. 7 is a zoomed-in version of the plot of FIG. 6. In both plots, the X-axis is frequency (Hz) and Y-axis is magnitude (dB). With reference to the Kovtun-Ricci wavelets, design parameters for this example are $N_k$=4, $N_m$=4 without loss of generality (sometimes abbreviated as w.l.o.g., this is intended to mean that in other embodiments of the invention, other suitable parameters are used).

Responses are normalized to have substantially 0 dB (unity gain) at the response peak, being the analytic frequency of the wavelet ("actual center frequency" 2512.1 per FIG. 3.1). This bank has the center frequencies spaced relatively closely—in this example, without loss of generality, approximately a nominal spacing of 18 bands per octave.

In some embodiments, the spacing, in combination with the bandwidths of the bandpasses, is chosen such that the responses cross at roughly −0.01 dB, generally a small number, so that the analysis represents substantially high resolution in frequency (along the frequency axis), sufficient to resolve frequency of the underlying component to satisfy the accuracy demanded by the application. For this example, the data sample rate $F_s$=200 Hz without loss of generality.

The table 3000 of FIG. 8 shows values for the wavelets for this example bank. As the bank is intended, for this example, to resolve a heart rate, the analytic frequencies of the wavelets are chosen to cover a range corresponding to the range of heart rates expected under physiological conditions (normal rest to exercise), without loss of generality.

The column labeled "R" shows the analytic frequencies in units of beats per minute (BPM), corresponding to heart rate. The column labeled $f_A$ shows the same analytic frequencies in units of Hz (Hertz, or cycles per second). The column $k_r$ shows the values of Kovtun-Ricci wavelet scaled-difference scaling parameter $k_r$ for each wavelet bandpass of this example bank. The values are chosen to be even to ensure integer delays in the system. Values of Kovtun-Ricci wavelet scaled-difference scaling parameter w for each band are set to $k_r/2$ in this example bank. This provides example bank as per bank 2400 of FIG. 2 or bank 2600 of FIG. 4 or bank 2700 of FIG. 5.

For input signal X, the bank performs an analysis whereby components in X will excite the bands to varying degrees. Periodicities in X closest to the response peaks of certain bands will excite them the most, so they are expected to have the largest local amplitude.

Figure 9:
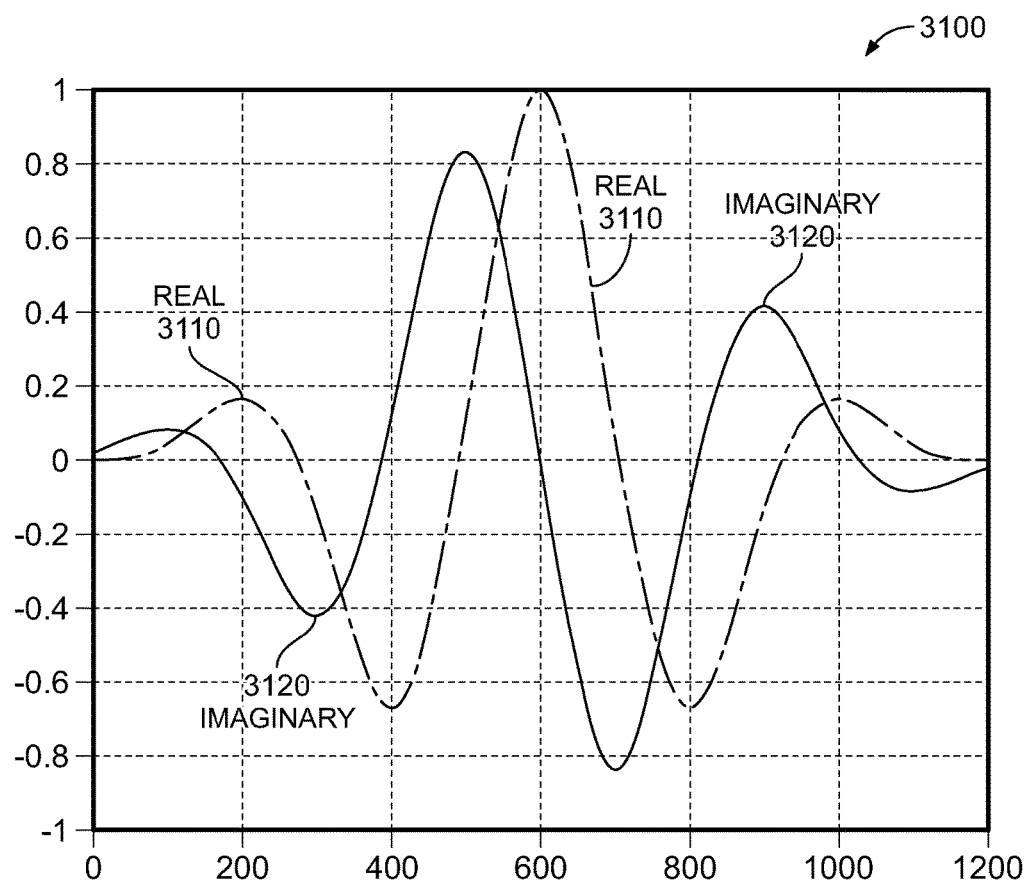
FIG. 9 is a graph 3100 of the real portion 3110 and imaginary portion 3120 of a wavelet impulse response, according to some embodiments of the present invention.

FIG. 9 is a plot 3100 of an example impulse response $L_K$ of an analytic wavelet band as per the description in U.S. Pat. No. 7,702,502, which issued on Apr. 20, 2010 titled "APPARATUS FOR SIGNAL DECOMPOSITION, ANALYSIS AND RECONSTRUCTION," and which is incorporated herein by reference. Trace 3110 is the real part of the impulse response; the imaginary part is trace 3120. The Y-axis is the impulse-response coefficient; the X-axis is the time index in samples. This response corresponds to the lowest-frequency band (r=1, $k_r$=200) in the list 3000 of FIG. 8 for the example bank, without loss of generality.

Other bands would be scaled versions of this response according to wavelet principles well-understood in the art and established also in Appendix A of the inventor's U.S. Provisional Patent Application 60/656,630, filed Feb. 23, 2005, titled "SYSTEM AND METHOD FOR SIGNAL DECOMPOSITION, ANALYSIS AND RECONSTRUCTION," and U.S. Pat. No. 7,702,502, which claimed benefit of U.S. Provisional Patent Application 60/656,630, both of which are incorporated herein by reference in its entirety.

Flow of Processing Example

Referring to FIG. 2, Input signal x 2401 is operated on in parallel by the wavelets 2406 in the bank 2412. The respective analytic outputs 2404 are then used by respective QP operators 2410 to form a set of fractional-phase representations 2409 of each (in some embodiments, a quarter-phase representation is formed, without loss of generality).

FIG. 10 is a listing of MATLAB code 3200 to implement QP transformation from analytic wavelet output $y_n$ (passed in is a complex-valued input argument x here). Output is sequence of QP object stream information: Lqp is a stream of QP labels (encoding A, B, C, and D here as 1, 2, 3, and 4, respectively) so that each element of vector Lqp is a single label for a single sequential QP object. Similarly, output iqp is the corresponding stream of QP time indexes of each of the corresponding QP objects, where a value of iqp corresponds to a sample time index into input vector x. Output aqp is the corresponding stream of QP object amplitudes, such that each element of vector aqp corresponds to the instantaneous amplitude of analytic signal X (here, analytic input signal vector x) at corresponding QP point iqp.

FIG. 11 (which includes FIG. 11.1, FIG. 11.2, and FIG. 11.3 taken together) is a listing of MATLAB code 3300 to implement QP transformation similarly to that of function 3200 shown in FIG. 10 except that the values of iqp and aqp are interpolated at the QP points of analytic signal x. Specifically, at the appropriate zero-crossings, the x-intercept is solved for, providing a more accurate measure of iqp. In some embodiments, a linear interpolation is performed based on the values straddling the zero crossing to solve for the time of the zero crossing. Using a linear model is accurate in practice because near X=0, sin(X)=X is a good approximation.

Correspondingly, the value of aqp is then linearly interpolated at the more-accurate value of iqp. Higher-order interpolations or fits can certainly be considered for these interpolation operations as part of this invention as they are well understood in the art. (For both functions 3200 and 3300 of FIG. 10 and FIG. 11, output argument Msem is not used in this embodiment.)

In some embodiments, if one considers the transform of signal x 2401 (as described above for FIG. 2, FIG. 5 and FIG. 6) as the parallel wavelet operation resulting in the series of signals $y_n$, n=1 . . . N, we can construct matrix Y as the appending of signals $y_n$, each a being column, appended column-wise. We assume here, without loss of generality, that the intrinsic delays of the wavelets in the banks are compensated so that the outputs are time-aligned (as described on p. 78 of Appendix A in U.S. Provisional Patent Application 60/656,630, filed Feb. 23, 2005, titled "SYSTEM AND METHOD FOR SIGNAL DECOMPOSITION, ANALYSIS AND RECONSTRUCTION," which is incorporated herein by reference in its entirety). We can then operate on matrix Y to produce the QP transformation. The code 3400 in FIG. 12 does this by repetitively (iteratively) calling either function getCmpQp( ) or function getCmpQpItp( ) on each column of Y, as chosen through logical variable ITP. (Matrix Y is passed in here as matrix input argument X.)

Output sObj is a structure array (an array of structs). Each element of sObj is itself a structure containing fields Lqp, iqp, and aqp, the QP object stream data as output by the functions shown in FIG. 10 or FIG. 11. Array sObj is indexed by the band, so that the nth element sObj(n) contains the QP information corresponding to signal $y_n$, of the set of signals $Y_n$, n=1 . . . M.

The code 3500 (MATLAB function trkMxQpA) in FIG. 13 performs the processing to resolve the desired component by maximum instantaneous amplitude. It works by advancing time until a wavelet output encounters a QP transition, then updates the "state" accordingly. The "state" here is considered as a vertical linking as described/contemplated in Book 1 pages 3-8 in Appendix A of the inventor's U.S. Provisional Patent Application 60/656,630, and FIGS. 7A, 7B, 7C, and 7D and their description in U.S. Pat. No. 7,702,502, which claimed benefit of U.S. Provisional Patent Application 60/656,630, both of which are incorporated herein by reference in their entirety. So, for sake of this example embodiment, vertical linking occurs across band index ib indexing sObj(ib). At each state update, the maximum-amplitude band is found and the corresponding QP information is stored in vector abmx, imbx, Lbmx and ixqp. These vectors are then stored as fields at the end into output structure sQpCmp.

In FIG. 13:

abmx=amplitude of highest-amplitude wavelet at state nqp;
ibmx=band index corresponding to abmx;
Lbmx=QP label corresponding to abmx;
ixqp=time index of original signal at corresponding state updates; and
sQpCmp.aqp, sQpCmp.Lqp, and sQpCmp.iqp=QP parameters of desired components (dominant components) over frequency band covered by wavelet bank.

For some types of signals x, the energy is very pulsatile, for example with ECG signals, such that the signal has a large crest factor. Being quasi-periodic, the signal is thus very "spiky" in its waveshape. This can cause ambiguity in the wavelet output amplitude—where the higher-frequency wavelets are excited more during the spike that during the dwell time. ("Ripples" are produced in the amplitude sequence aqp for the higher frequency wavelets.) This causes biases in the selection of the band based upon amplitude, where the band selection gets skewed upward during the time locally surrounding the "spikes."

In one embodiment, the solution would be to increase the order $N_k$ of the derivative band of the wavelets. Other embodiments would seek to process the amplitude sequence aqp to remove/suppress the ripples of aqp due to the input spikes.

The function flpsQpA.m 3600 in FIG. 14 performs smoothing (low-pass filtering) of the sequences sObj(ib) .aqp. In this embodiment an integral-kernel wavelet operates on the aqp sequence corresponding to each $ib^{th}$ band. The integral-kernel wavelet smoother, called here through MATLAB function flpsfilt( ) is as per operator hq( ) on page 66 of Book 1 in Appendix A of the inventor's U.S. Provisional Patent Application 60/656,630, and FIGS. 7A, 7B, 7C, and 7D and their description in U.S. Pat. No. 7,702,502, which claimed benefit of U.S. Provisional Patent Application 60/656,630, both of which are incorporated herein by reference in their entirety, with N-order variable No here corresponding to $N_m$ on p. 66 of Book 1 and wQP here corresponding to $N_w$ for hq as per p. 66 of Book 1. Scale wQP is scaled to correspond to a nominal time, though in some embodiments it may be a constant with respect to band number. Here the "fixed-time" scaling is accomplished through input argument T (in seconds) along with analytic (center) frequency parameter vector "fan" (in Hz) for each band. Thus wQP is a vector, in units of number of quarter-phases approximating time T for each band. Operator No is the order, and is arbitrary (usually a nominal value of No=2 is used). Output aqpm is the smoothed amplitude sequence and stored back to sObj as a new field for each corresponding band. The new smoothed amplitude sequence may then be used for estimating the center of a narrower band range over which to track the desired component.

The function trkMxQpAGrd 3700 (MATLAB code) in FIG. 15.1-15.2 implements modified tracking, it operates similar to the code 3500 in FIG. 13, except it first identifies a band range using aqpm, at each state update, before then finding the max of aqp over that restricted band range.

The state of aqpm is stored on state variable aqpmSt and the state of aqp is stored in state variable aqpSt. The resulting tracked component information is output as before, with additional tracked information from aqpm output in second output structure as sQpCmpm. As before in code 3500 in FIG. 13, the desired component QP information is contained in structure sQpCmp fields aqp, ibqp, and iqp and this forms the "QP stream" for this component.

Figure 16:
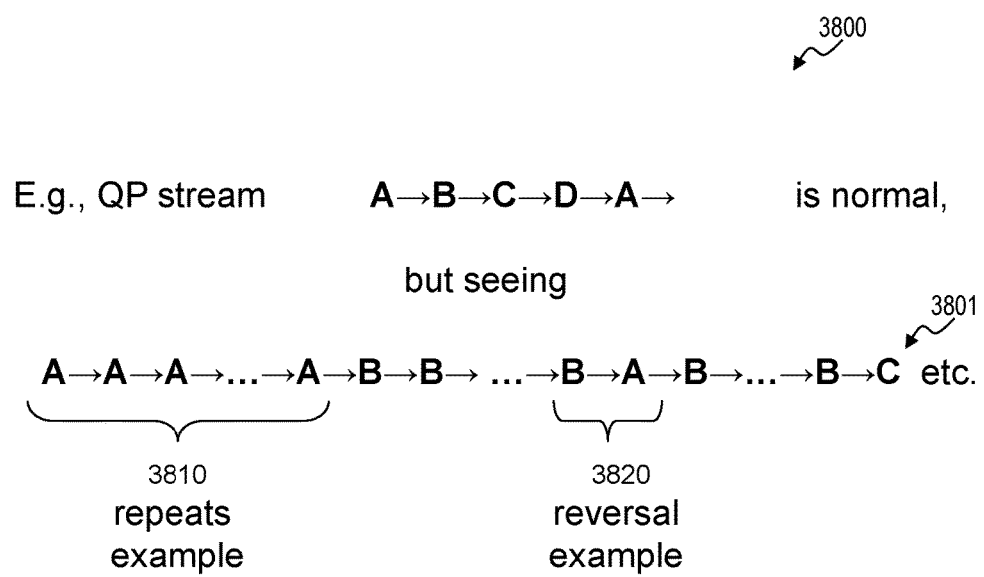
FIG. 16 shows examples sequences of QP labels, with an expected sequence 3800 and a sequence 3801 with disturbances, according to some embodiments of the present invention.

FIG. 16 shows example QP streams 3800. The resulting QP stream 3801 can in some embodiments contain repeated labels 3810 for many consecutive state updates, sometimes interspersed with "phase reversals" 3820 (reversed in the expected forward pattern of labels).

The code 3900 in FIGS. 17.1-17.2 works to both collect all repeats into a single QP of that label, and to also remove phase reversals. Collection of repeats deletes and collapses the label repeat and takes an amplitude-weighted average of the indices (both time and band indices) and an average of the amplitude for each epoch of sequential repeated labels. The result is a cleaned sequence of QP objects, useful for further analysis, storage, or reconstruction as per all of Book 1 in Appendix A of the inventor's U.S. Provisional Patent Application 60/656,630, and pp. 1-20 of Appendix B of the inventor's U.S. Provisional Patent Application 60/656,630.

In some embodiments, the present invention uses techniques as described, in particular in paragraphs [0054]-[0060] of the application (columns 6-8 of the issued patent), and elsewhere in U.S. Pat. No. 7,702,502, which is incorporated herein by reference.

In some embodiments, the present invention demodulates the fractional phase components (e.g., QP outputs 2429 of FIG. 2) of the tracked component. In some embodiments, the demodulator unit demodulates the amplitude (using amplitude (AM) demodulation) and/or the instantaneous frequency sequence (using frequency (FM) demodulation) to give the AM and FM variability of the tracked signal. In some embodiments, this demodulated signal; e.g., heart rate physiological parameters are important.

In some embodiments, the amplitude and frequency sequences of the QP outputs 2429 are treated as signals and a transform unit performs a transform (e.g., a wavelet or other suitable transform such as a Walsh transform), and performs an analysis in transform domain, wherein the wavelet scale corresponds to the "sequency" of the QP signals.

In some embodiments, the sequency peaks are measured to determine sequency content. In some embodiments, the present invention graphs the amplitudes and frequencies of the QPs 2429 of the tracked component (QP periods updated every ¼ phase) and/or runs a transform to find energy at different frequencies or sequencies.

Figure 18:
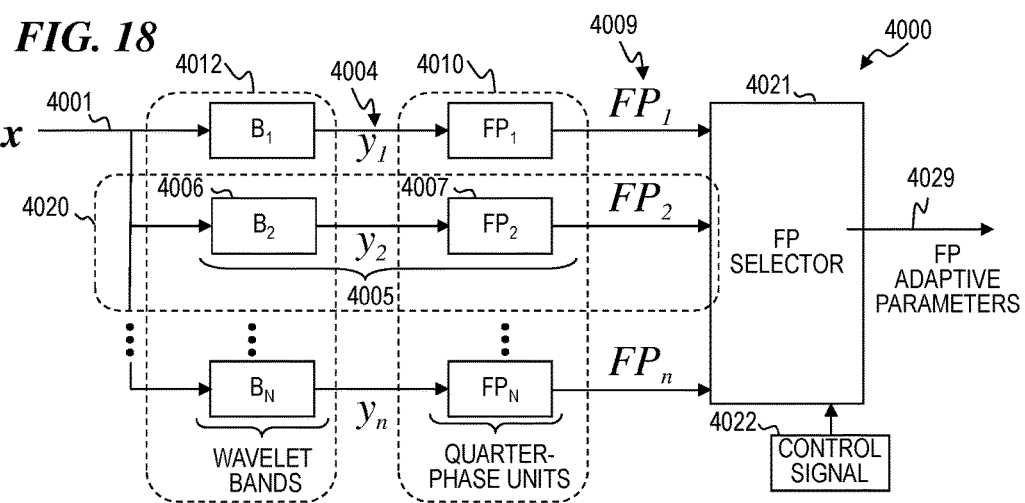
FIG. 18 is a block diagram of a subsystem 4000 used to track one component over a wide range of frequencies by an adaptive selection of a selected frequency band from among a bank of overlapping frequency bands within the signal decomposition function 2302 of FIG. 1.2 and the fractional-phase representation function 2303, according to some embodiments of the present invention.

FIG. 18 is a block diagram of a method and apparatus for processing FP parameters to obtain adaptive parameters useful for tracking varying frequency components, wherein x=digitized input signal 4001, $B_1, B_2, \ldots B_N$=Wavelet filters bank 4012,
$FP_1, FP_2, \ldots FP_N$=a bank of quarter-phase generators 4010 corresponding to each frequency band 4006,
$FP_1, FP_2, \ldots FP_N$=a set of streams of quarter-phase parameters 4009 corresponding to each frequency band.

In some embodiments, FP selector 4021 is controlled by a selection (control) signal 4022 and selects, at given point in time, one FP stream of the set of FP streams: $FP_1, FP_2 \ldots FP_N$.

In some embodiments, selection signal 4022 may indicate the band having the maximum power or amplitude from among the bands operating on signal x 4001, where a band having maximum amplitude means one of the bands having an amplitude no lower than the other bands in the associated bank. (For purposes of generating the selection or indication signal, the terms "maximum-power" and "maximum-amplitude" are to be used interchangeably.) In some embodiments, selection signal 4022 may indicate the band having the maximum power or amplitude from among the bands operating on another signal, or in another frequency range. In some embodiments, by associating the maximum-amplitude band indication with the band's center frequency, an estimate of the component frequency is formed, and used as a frequency estimate signal.

In some embodiments, selection signal 4022 indicates a plurality of the bands from which an interpolation can be made from amplitudes of bands surrounding the band having the maximum amplitude. In some embodiments (where two bands could possibly have the same maximum amplitude), the present invention selects one of the bands that has an amplitude no lower than the other bands in the bank (i.e., one of the banks having the maximum amplitude). In some embodiments, the center frequencies of the bands form the x-values of the points to be interpolated, and the associated band amplitudes form the y-values of the points to be interpolated, for example, through a curve fit or a spline. In some embodiments, the interpolation is in the form of a polynomial fit, with a fit of polynomial order N requiring at least N+1 point values (and thus at least N+1 bands including the maximum-amplitude band). In some embodiments, a second-order polynomial (parabolic) fit is performed, as the convex parabola has a single well-defined peak and a shape consistent with an amplitude peak. The parabolic fit would thus require at least three point values. Performing the parabolic fit and solving for the peak of the (convex) parabola results in an amplitude value and frequency value that estimate respectively the amplitude and frequency of the frequency component, with higher resolution than estimates formed from simple selection of the maximum-amplitude band.

See the illustrative discussion of curve fitting for FIG. 3.3.

In some embodiments the x-values of the fit are formed from indices corresponding to the ordered position of the respective bands. Performing the parabolic fit and solving for the peak then results in an interpolated index. In some embodiments the interpolated index can be mapped to the band frequencies through a mapping function or interpolated table lookup to determine an associated frequency. In some embodiments the interpolated index may be used along with the FP values of the bands whose indices straddle the interpolated index, to form an interpolated FP value with a higher-resolution than either of the direct FP values from the bands.

In some embodiments, the band frequencies of the filters are spaced logarithmically, and the instantaneous frequency is determined by interpolating upon the logarithms of the band frequencies.

In some embodiments of the invention shown in FIG. 18, the fractional phases are quarter phases. In other embodiments, other fractional phases are used.

In some embodiments, the present invention uses the same plurality of digital bandpass filters to obtain the signals used to derive the selection signal (e.g., selection signal 2422 of FIG. 2) as is used to obtain the quarter-phase representations that the selection signal is applied to in order to get the tracked signal, such that the same bandwidth and same center frequencies are used to get the selection signal and to provide the data streams that are selected. In other embodiments, a different plurality of digital bandpass filters to obtain the signals used to derive the selection signal (e.g., selection signal 2422 of FIG. 2), wherein the plurality of selection-signal source inputs have a different set of bandwidths and/or a different set of center frequencies as is used to obtain the quarter-phase representations that the selection signal is applied to in order to get the tracked signal, such that different bandwidths and/or different center frequencies are used to get the selection signal as are used to provide the data streams that are selected. In still other embodiments, the selection signal is derived using some other process than determining one or more maximum amplitudes from a plurality of bandpass-filtered signals and/or their fractional-phase (e.g., quarter-phase) representations.

In some embodiments, the selection signal provides a plurality of selection indications such that a plurality of data streams is selected. In some embodiments, the plurality of data streams are interpolated to obtain an "instantaneous" tracked frequency that is updated once per data cycle (the rate that the values $y_N$ arrive), or once per quarter phase (the rate at which the time values of $QP_N$ are updated), or once per full cycle of the tracked component (the rate at which the $QP_N$ full-cycle (ABCD) objects updated), or at some other rate.

In some embodiments, the present invention provides an apparatus that includes a computer having a storage device; a source of an initial series of digitized signal values; a first filter bank that includes a first plurality of digital bandpass filters each operably coupled to the source of digitized signal values and each configured to digitally filter the initial series of digitized signal values, wherein each one of the first plurality of digital bandpass filters has a respective center frequency that is unique among respective center frequencies of the first plurality of digital bandpass filters and a respective frequency range that overlaps the respective frequency range of a closest neighboring one of the first plurality of digital bandpass filters (i.e., the next-door neighbor's frequency range), and wherein each one of the first plurality of digital bandpass filters has an output signal; and a first frequency-component tracker that uses the output signals from the plurality of digital bandpass filters to detect and track a first frequency component as that first frequency component's main component moves from one to another frequency range of the first plurality of digital bandpass filters, and to store information regarding the tracked frequency component into the storage device.

In some embodiments, the present invention provides an apparatus that includes: a computer having a storage device; a source of an initial series of digitized signal values; a first filter bank that includes a first plurality of digital bandpass filters each operably coupled to the source of digitized signal values and each configured to digitally filter the initial series of digitized signal values, wherein each one of the first plurality of digital bandpass filters has a respective center frequency that is unique among respective center frequencies of the first plurality of digital bandpass filters and a respective frequency range, and wherein each one of the first plurality of digital bandpass filters has an output signal; a first plurality of fractional-phase measurement units that each determines a plurality of amplitude values and a plurality of phase-determined time points per full waveform cycle of the output signal of a corresponding one of the first plurality of digital bandpass filters; and a first frequency-component tracker that uses the plurality of amplitude values from the first plurality of fractional-phase measurement units to detect and track a first frequency component as that first frequency component's frequency moves from one to another frequency range of the first plurality of digital bandpass filters, and to store information regarding the tracked frequency component into the storage device, wherein the stored information includes instantaneous frequency and amplitude of the tracked frequency component at each of a first sequence of time points. In some embodiments, the first sequence of time points include interpolated time points derived from the plurality of phase-determined time points from the first plurality of fractional-phase measurement units.

In some embodiments of the apparatus, the first filter bank includes at least four digital bandpass filters per octave of frequency. In some embodiments of the apparatus, the first filter bank includes at least six digital bandpass filters per octave of frequency. In some embodiments of the apparatus, the first filter bank includes at least eight digital bandpass filters per octave of frequency. In some embodiments of the apparatus, the first filter bank includes at least twelve digital bandpass filters per octave of frequency. In some embodiments of the apparatus, the first filter bank includes at least sixteen digital bandpass filters per octave of frequency. In some embodiments of the apparatus, the first filter bank includes at least twenty digital bandpass filters per octave of frequency.

In some embodiments, the first filter bank includes the first plurality of digital bandpass filters whose center frequencies are spaced relative to one another based on a logarithmic scale. In some embodiments, the first filter bank includes digital bandpass filters whose center frequencies are spaced relative to one another based on a linear scale. In some embodiments, the first filter bank includes digital bandpass filters whose center frequencies are spaced relative to one another based on some other suitable scale. In some embodiments, an entire range of center frequencies of the first plurality of digital bandpass filters are spaced according to a logarithmic scale.

In some embodiments of the apparatus, the first filter bank includes digital bandpass filters that have center frequencies that cover a range of frequencies of at least one octave (i.e., a range of frequencies of at least 2:1). In some embodiments of the apparatus, the first filter bank includes digital bandpass filters that have center frequencies that cover a range of frequencies of at least 3:1. In some embodiments of the apparatus, the first filter bank includes digital bandpass filters that have center frequencies that cover a range of frequencies of at least two octaves (i.e., a range of frequencies of at least 4:1). In some embodiments of the apparatus, the first filter bank includes digital bandpass filters that have center frequencies that cover a range of frequencies of at least 5:1. In some embodiments of the apparatus, the first filter bank includes digital bandpass filters that have center frequencies that cover a range of frequencies of at least 6:1. In some embodiments of the apparatus, the first filter bank includes digital bandpass filters that have center frequencies that cover a range of frequencies of at least 7:1. In some embodiments of the apparatus, the first filter bank includes digital bandpass filters that have center frequencies that cover a range of frequencies of at least three octaves (i.e., a range of frequencies of at least 8:1). In some embodiments of the apparatus, the first filter bank includes digital bandpass filters that have center frequencies that cover a range of frequencies of at least 10:1. In some embodiments of the apparatus, the first filter bank includes digital bandpass filters that have center frequencies that cover a range of frequencies from about 30 cycles per minute to at least 300 cycles per minute (in this case, a range of 10:1). In some embodiments of the apparatus, the first filter bank includes digital bandpass filters that have center frequencies that cover a range of frequencies from about 40 cycles per minute to at least 280 cycles per minute (in this case, a range of 7:1). In some embodiments of the apparatus, the first filter bank includes digital bandpass filters that have center frequencies that are spaced across a range of frequencies from about 40 cycles per minute to at least 240 cycles per minute (in this case, a range of 6:1). In some embodiments of the apparatus, the first filter bank includes digital bandpass filters that have center frequencies that are spaced across a range of frequencies from about 50 cycles per minute to at least 250 cycles per minute (in this case, a range of 5:1). In some embodiments of the apparatus, the first filter bank includes digital bandpass filters that have center frequencies that are spaced across a range of frequencies from about 30 cycles per minute to at least 240 cycles per minute (in this case, a range of 8:1). In some embodiments of the apparatus, the first filter bank includes digital bandpass filters that have center frequencies that are spaced across a range of frequencies from about 50 cycles per minute to at least 200 cycles per minute (in this case, a range of 4:1).

In some embodiments, the initial digitized signal x 2401 is obtained from a physiological signal sensed from a human, and in some such embodiments, from an electrocardiogram signal.

In some embodiments of the apparatus, each one of the first plurality of digital bandpass filters includes a wavelet-transform filter.

In some embodiments of the apparatus, the first frequency-component tracker further includes a fractional-phase measurement unit that determines at least two amplitude values, at least one phase-determined time point per full waveform cycle of the first tracked frequency component, and a per-unit-time center frequency indication of the first tracked frequency component for each respective unit of time of the first tracked frequency component.

In some embodiments of the apparatus, the first frequency-component tracker further includes an output quarter-phase measurement unit that determines at least two amplitude values and at least four phase-determined time points per full waveform cycle of the first tracked frequency component, and that outputs a first series of respective data structures that each indicates the at least two amplitude values, the at least four phase-determined time points per respective full waveform cycle of the first tracked frequency component, and a per-cycle center frequency of the first tracked frequency component for the respective full waveform cycle of the first tracked frequency component.

In some embodiments of the apparatus, the first frequency-component tracker further includes a first quarter-phase bank that includes a first plurality of quarter-phase measurement units, each of which determines at least two amplitude values and at least four phase-determined time points per full waveform cycle of a corresponding one of the first plurality of digital bandpass filters; a quarter-phase maximum-amplitude determination unit that determines which one of the first plurality of quarter-phase measurement units had an amplitude value no lower than did any other one of the first plurality of quarter-phase measurement units during a time period (i.e., the quarter-phase object having maximum amplitude) and that outputs a selection signal based on the determination; and a first selector that selects information from one of first plurality of quarter-phase measurement units based on the selection signal, and outputs the selected information and an indication of the center frequency of the corresponding one of the first plurality of digital bandpass filters. In some such embodiments, the selection signal is based on one or more frequencies of the corresponding one or more of the first plurality of digital bandpass filters, and is determined by interpolation. In some such embodiments, the quarter-phase maximum-amplitude determination unit further includes a data smoother that smooths amplitude values from each of the first plurality of quarter-phase measurement units before the quarter-phase maximum-amplitude determination unit determines which one of the first plurality of quarter-phase measurement units has the amplitude value no lower than did any other one of the first plurality of quarter-phase measurement units during a time period. In some such embodiments, the first quarter-phase bank further includes a data smoother that smooths amplitude values from each of the first plurality of digital bandpass filters before the first quarter-phase bank determines and outputs at least two amplitude values and at least four phase-determined time points per full waveform cycle of an output of the corresponding one of the first plurality of digital bandpass filters.

In some embodiments of the apparatus, the first frequency-component tracker further includes a maximum-amplitude determination unit that determines which one of the first plurality of first plurality of digital bandpass filters had an amplitude value no lower than did any other one of the first plurality of digital bandpass filters during a time period and that outputs a selection signal based on the determination; and a first selector that selects information from one of first plurality of digital bandpass filters based on the selection signal, and outputs the selected information and an indication of the center frequency of the selected one of the first plurality of digital bandpass filters.

In some embodiments of the apparatus, the first frequency-component tracker further includes a maximum-amplitude determination unit that determines which one of the first plurality of first plurality of digital bandpass filters had an amplitude value no lower than did any other one of the first plurality of digital bandpass filters during a time period and that outputs a selection signal based on the determination; a first selector that selects information from one of first plurality of digital bandpass filters based on the selection signal, and outputs the selected information and an indication of the center frequency of the selected one of the first plurality of digital bandpass filters; and a fractional-phase measurement unit that determines at least two amplitude values and at least one phase-determined time point per full waveform cycle of the tracked frequency component.

In some embodiments of the apparatus, the first frequency-component tracker further includes a maximum-amplitude determination unit that determines which one of the first plurality of digital bandpass filters had an amplitude value no lower than did any other one of the first plurality of digital bandpass filters during a time period and that outputs a selection signal based on the determination; a first selector that selects information from one of first plurality of digital bandpass filters based on the selection signal, and outputs the selected information and an indication of the center frequency of the selected one of the first plurality of digital bandpass filters; and a quarter-phase measurement unit that determines at least two amplitude values and at least four phase-determined time points per full waveform cycle of the tracked frequency component. In some such embodiments, the quarter-phase maximum-amplitude determination unit further includes a data smoother that smooths amplitude values from each of the first plurality of quarter-phase measurement units before the quarter-phase maximum-amplitude determination unit determines which one of the first plurality of quarter-phase measurement units has the amplitude value no lower than did any other one of the first plurality of quarter-phase measurement units during a time period. In some such embodiments, the first quarter-phase bank further includes a data smoother that smooths amplitude values from each of the first plurality of digital bandpass filters before the first quarter-phase bank determines and outputs at least two amplitude values and at least four phase-determined time points per full waveform cycle of an output of the corresponding one of the first plurality of digital bandpass filters.

In some embodiments of the apparatus, each one of the first plurality of digital bandpass filters is a wavelet-transform filter; and the first frequency-component tracker further includes: a first quarter-phase bank that includes a first plurality of quarter-phase measurement units, each of which determines at least two amplitude values and at least four phase-determined time points per full waveform cycle of a corresponding one of the first plurality of digital bandpass filters; a first quarter-phase maximum-amplitude determination unit that determines which one of the first plurality of quarter-phase measurement units had an amplitude value no lower than did any other one of the first plurality of quarter-phase measurement units during a time period and that outputs a selection signal based on the determination; and a first selector that selects information from one of first plurality of quarter-phase measurement units based on the selection signal, and outputs the selected information and an indication of the center frequency of the corresponding one of the first plurality of digital bandpass filters.

In some embodiments of the apparatus, each one of the first plurality of digital bandpass filters is a wavelet-transform filter; and wherein the first frequency-component tracker further includes: a first quarter-phase bank that includes a first plurality of quarter-phase measurement units, each of which determines at least two amplitude values and at least four phase-determined time points per full waveform cycle of a corresponding one of the first plurality of digital bandpass filters; a quarter-phase maximum-amplitude determination unit that determines which one of the first plurality of quarter-phase measurement units had an amplitude value no lower than did any other one of the first plurality of quarter-phase measurement units during a time period and that outputs a selection signal based on the determination; and a selector that selects information from one of first plurality of quarter-phase measurement units based on the selection signal, and outputs the selected information and an indication of the center frequency of the corresponding one of the first plurality of digital bandpass filters, and the apparatus further includes a third plurality of digital bandpass filters, wherein each one of the third plurality of digital bandpass filters has a center frequency that is unique among the third plurality of digital bandpass filters, wherein each one of the third plurality of digital bandpass filters is a wavelet-transform filter, and wherein each one of the third plurality of digital bandpass filters has an output signal; a third plurality of quarter-phase measurement units operatively coupled to receive the output signals from the third plurality of digital bandpass filters, wherein each of the third plurality of quarter-phase measurement units determines and outputs at least two amplitude values and at least four phase-determined time points per full waveform cycle of a corresponding one of the third plurality of digital bandpass filters.

Some embodiments of the apparatus further include a second plurality of digital bandpass filters, wherein each one of the second plurality of digital bandpass filters has a respective center frequency that corresponds to the respective center frequency of one of the first plurality of digital bandpass filters and a frequency range that is narrower than the frequency range of the respective frequency range of the one of the first plurality of digital bandpass filters, wherein each one of the second plurality of digital bandpass filters is a wavelet-transform filter, and wherein each one of the second plurality of digital bandpass filters has an output signal; a second plurality of quarter-phase measurement units operatively coupled to receive the output signals from the second plurality of digital bandpass filters, wherein each of the second plurality of quarter-phase measurement units determines at least two amplitude values and at least four phase-determined time points per full waveform cycle of a corresponding one of the second plurality of digital bandpass filters (in some embodiments, this second plurality of digital bandpass filters and the corresponding second plurality of quarter-phase measurement units are used to derive the selection signal applied to the selector discussed below); wherein each one of the first plurality of digital bandpass filters is a wavelet-transform filter; and wherein the first frequency-component tracker further includes: a first quarter-phase bank that includes a first plurality of quarter-phase measurement units, each of which determines at least two amplitude values and at least four phase-determined time points per full waveform cycle of a corresponding one of the first plurality of digital bandpass filters; a quarter-phase maximum-amplitude determination unit that determines which one of the second plurality of quarter-phase measurement units had an amplitude value no lower than did any other one of the second plurality of quarter-phase measurement units during a time period and that outputs a selection signal based on the determination; a selector that selects information from one of first plurality of quarter-phase measurement units based on the selection signal, and outputs the selected information and an indication of the center frequency of the corresponding one of the first plurality of digital bandpass filters (e.g., the second plurality of digital bandpass filters and/or the second plurality of quarter-phase measurement units are used to derive the selection signal, which is used by the tracker-selector, from the maximum amplitude of the outputs of these filters or these QP units); and a third plurality of digital bandpass filters, wherein each one of the third plurality of digital bandpass filters has a center frequency that is unique among the third plurality of digital bandpass filters, wherein each one of the third plurality of digital bandpass filters is a wavelet-transform filter, and wherein each one of the third plurality of digital bandpass filters has an output signal; a third plurality of quarter-phase measurement units operatively coupled to receive the output signals from the third plurality of digital bandpass filters, wherein each of the third plurality of quarter-phase measurement units determines at least two amplitude values and at least four phase-determined time points per full waveform cycle of a corresponding one of the third plurality of digital bandpass filters. In some embodiments, the third plurality of digital bandpass filters and the third plurality of quarter-phase measurement units are not used to track components of the signal x, since in some embodiments, the frequencies of these components do not widely vary in frequency.

In other embodiments, the present invention provides has a fixed bank that provides QP objects at frequencies that are not processed to track components as those components move from the frequency band of one digital bandpass filter to that of its neighbor.

Some embodiments of the apparatus further include a second plurality of digital bandpass filters, wherein each one of the second plurality of digital bandpass filters has a respective center frequency that corresponds to the respective center frequency of one of the first plurality of digital bandpass filters and a frequency range that is narrower than the frequency range of the respective frequency range of the one of the first plurality of digital bandpass filters, wherein each one of the second plurality of digital bandpass filters is a wavelet-transform filter, and wherein each one of the second plurality of digital bandpass filters has an output signal; a second plurality of quarter-phase measurement units operatively coupled to receive the output signals from the second plurality of digital bandpass filters, wherein each of the second plurality of quarter-phase measurement units determines and outputs a series of QP objects, wherein each one of the series of QP objects has at least two amplitude values and at least four phase-determined time points per full waveform cycle of a corresponding one of the second plurality of digital bandpass filters; and wherein each one of the first plurality of digital bandpass filters is a wavelet-transform filter; and wherein the first frequency-component tracker further includes: a first quarter-phase bank that includes a first plurality of quarter-phase measurement units, each of which determines at least two amplitude values and at least four phase-determined time points per full waveform cycle of a corresponding one of the first plurality of digital bandpass filters; a quarter-phase maximum-amplitude determination unit that determines which one of the second plurality of quarter-phase measurement units had an amplitude value no lower than did any other one of the second plurality of quarter-phase measurement units during a time period and that outputs a selection signal based on the determination; and a selector that selects information from one of first plurality of quarter-phase measurement units based on the selection signal, and outputs the selected information and an indication of the center frequency of the corresponding one of the first plurality of digital bandpass filters.

In some embodiments, the present invention provides a computer-implemented method that includes: digitally filtering an initial series of digitized signal values in a computer to generate a first plurality of digitally bandpass filtered signals, wherein each one of the first plurality of digitally frequency filtered signals has a respective center frequency that is unique among respective center frequencies of the first plurality of digitally frequency filtered signals and a respective frequency range that overlaps the respective frequency range of a closest neighboring one of the first plurality of digitally frequency filtered signals; using the first plurality of digitally frequency filtered signals for detecting and tracking, in the computer, a first frequency component as that first frequency component's main component moves from one to another frequency range of the first plurality of digitally frequency filtered signals; and storing information regarding the tracked frequency component into a storage device.

In some embodiments of the computer-implemented method, the digitally filtering includes wavelet-transforming the initial series of digitized signal values to generate a plurality of wavelet-transformed signals.

In some embodiments of the computer-implemented method, the using of the first plurality of digitally frequency filtered signals for detecting and tracking the first frequency component further includes: determining and outputting at least two amplitude values, at least one phase-determined time point per full waveform cycle of the first tracked frequency component, and a per-unit-time center frequency indication of the first tracked frequency component for each respective unit of time of the first tracked frequency component.

In some embodiments of the computer-implemented method, the using of the first plurality of digitally frequency filtered signals for detecting and tracking the first frequency component further includes: determining at least two amplitude values and at least four phase-determined time points per full waveform cycle of the first tracked frequency component, and outputting a first series of respective data structures that each indicates the at least two amplitude values, the at least four phase-determined time points per respective full waveform cycle of the first tracked frequency component, and a per-cycle center frequency of the first tracked frequency component for the respective full waveform cycle of the first tracked frequency component.

In some embodiments of the computer-implemented method, the using of the first plurality of digitally frequency filtered signals for detecting and tracking the first frequency component further includes: performing a first plurality of quarter-phase measurements, each of which determines at least two amplitude values and at least four phase-determined time points per full waveform cycle of a corresponding one of the first plurality of digitally frequency filtered signals, and outputting a resulting plurality of quarter-phase objects; performing a quarter-phase maximum-amplitude determination of which one of the first plurality of quarter-phase objects had an amplitude value no lower than did any other one of the first plurality of quarter-phase objects during a time period (i.e., the quarter-phase object having maximum amplitude during that time period) and outputting a selection signal based on the determination; and selecting information from one of first plurality of quarter-phase objects based on the selection signal, and outputting the selected information and an indication of the center frequency of the corresponding one of the first plurality of digitally frequency filtered signals. This selecting is based QP output. In some embodiments, the selecting is done each quarter period (four times per cycle), while in other embodiments, the selecting is done once per cycle, while in other embodiments, the selecting is done at other intervals.

In some embodiments of the computer-implemented method, the using of the first plurality of digitally frequency filtered signals for detecting and tracking the first frequency component further includes: determining which one of the first plurality of digitally frequency filtered signals had an amplitude value no lower than did any other one of the first plurality of digitally frequency filtered signals during a time period and outputting a selection signal based on the determination; and selecting information from one of first plurality of digitally frequency filtered output signals based on the selection signal, and outputting the selected information and an indication of the center frequency of the selected one of the first plurality of digitally frequency filtered signals. In these embodiments, this selecting is based on filter output rather than QP output. In some embodiments, the selecting is done once per $y_n$ cycle, while in other embodiments, the selecting is done at other intervals.

In some embodiments of the computer-implemented method, the using of the first plurality of digitally frequency filtered signals for detecting and tracking the first frequency component further includes: determining which one of the first plurality of first plurality of digitally frequency filtered signals had an amplitude value no lower than did any other one of the first plurality of digitally frequency filtered signals during a time period and outputting a selection signal based on the determination; selecting information from one of first plurality of digitally frequency filtered signals based on the selection signal, and outputting the selected information and an indication of the center frequency of the selected one of the first plurality of digitally frequency filtered signals; and performing a fractional-phase measurement that determines at least two amplitude values and at least one phase-determined time point per full waveform cycle of the tracked frequency component. In these embodiments, this selecting is based on filter output rather than QP output. In some embodiments, the selecting is done once per $y_n$ cycle, while in other embodiments, the selecting is done at other intervals.

In some embodiments of the computer-implemented method, the using of the first plurality of digitally frequency filtered signals for detecting and tracking the first frequency component further includes: determining which one of the first plurality of first plurality of digitally frequency filtered signals had an amplitude value no lower than did any other one of the first plurality of digitally frequency filtered signals during a time period and outputting a selection signal based on the determination; selecting information from one of first plurality of digitally frequency filtered signals based on the selection signal, and outputs the selected information and an indication of the center frequency of the selected one of the first plurality of digitally frequency filtered signals; and performing a quarter-phase measurement that determines and outputs at least two amplitude values and at least four phase-determined time points per full waveform cycle of the tracked frequency component. In these embodiments, this selecting is based on filter output rather than QP output. In some embodiments, the selecting is done once per $y_n$ cycle, while in other embodiments, the selecting is done at other intervals.

In some embodiments of the computer-implemented method, each one of the first plurality of digitally frequency filtered signals is a wavelet-transformed frequency filtered signal; and the using of the first plurality of digitally frequency filtered signals for detecting and tracking the first frequency component further includes: performing a first plurality of quarter-phase measurements, each of which determines at least two amplitude values and at least four phase-determined time points per full waveform cycle of a corresponding one of the first plurality of digital bandpass filters; determining which one of the first plurality of quarter-phase measurements had an amplitude value no lower than did any other one of the first plurality of quarter-phase measurements during a time period and outputting a selection signal based on the determination; and selecting information from one of first plurality of quarter-phase measurements based on the selection signal, and outputting the selected information and an indication of the center frequency of the corresponding one of the first plurality of digital bandpass filters. In these embodiments, this selecting is based QP output. In some embodiments, the selecting is done each quarter period (four times per cycle), while in other embodiments, the selecting is done once per cycle, while in other embodiments, the selecting is done at other intervals.

Some embodiments of the computer-implemented method and wherein each one of the first plurality of digitally frequency filtered signals is a wavelet-transformed frequency-filtered signal; and wherein the using of the first plurality of digitally frequency filtered signals for detecting and tracking the first frequency component further includes: performing a first plurality of quarter-phase measurements, each of which determines at least two amplitude values and at least four phase-determined time points per full waveform cycle of a corresponding one of the first plurality of digitally frequency filtered signals; determining which one of the first plurality of quarter-phase measurements had an amplitude value no lower than did any other one of the first plurality of quarter-phase measurements during a time period and outputting a selection signal based on the determination; and selecting information from one of first plurality of quarter-phase measurements based on the selection signal, and outputting the selected information and an indication of the center frequency of the corresponding one of the first plurality of digitally frequency filtered signals. These embodiment of the method further include digitally filtering the initial series of digitized signal values in a computer to generate a third plurality of digitally frequency filtered signals, wherein each one of the third plurality of digitally frequency filtered signals has a center frequency that is unique among the third plurality of digitally frequency filtered signals and a frequency range that overlaps the frequency range of a closest neighboring one of the third plurality of digitally frequency filtered signals, wherein each one of the third plurality of digitally frequency filtered signals is a wavelet-transformed frequency-filtered signal (these digitally frequency filtered signals are for non-tracked components); performing a third plurality of quarter-phase measurements, each of which determines at least two amplitude values and at least four phase-determined time points per full waveform cycle of a corresponding one of the third plurality of digitally frequency filtered signals (these quarter-phase measurements are for non-tracked components). In these embodiments, this selecting is based on QP output signals. In some embodiments, the selecting is done each quarter period (four times per cycle), while in other embodiments, the selecting is done once per cycle, while in other embodiments, the selecting is done at other intervals.

Some embodiments of the computer-implemented method further include digitally filtering the initial series of digitized signal values to generate a second plurality of digitally frequency filtered signals, wherein each one of the second plurality of digitally frequency filtered signals has a respective center frequency that corresponds to the respective center frequency of one of the first plurality of digitally frequency filtered signals and a frequency range that is narrower than the frequency range of the respective frequency range of the one of the first plurality of digitally frequency filtered signals, and wherein each one of the second plurality of digitally frequency filtered signals is a wavelet-transformed filtered signal (e.g., in some embodiments, this second plurality of digitally frequency filtered signals corresponds to the narrow-band filters graphed in FIG. 3.2); performing a second plurality of quarter-phase measurements on the second plurality of digitally frequency filtered signals, wherein each of the second plurality of quarter-phase measurements determines at least two amplitude values and at least four phase-determined time points per full waveform cycle of a corresponding one of the second plurality of digitally frequency filtered signals; wherein each one of the first plurality of digitally frequency filtered signals is a wavelet-transformed filtered signal; and wherein the using of the first plurality of digitally frequency filtered signals for detecting and tracking the first frequency component further includes: performing a first plurality of quarter-phase measurements, each of which determines at least two amplitude values and at least four phase-determined time points per full waveform cycle of a corresponding one of the first plurality of digitally frequency filtered signals (e.g., in some embodiments, this maximum so from the second plurality of digitally frequency filtered signals that corresponds to the narrow-band filters graphed in FIG. 3.2); determining which one of the first plurality of quarter-phase measurements an amplitude value no lower than did any other one of the first plurality of quarter-phase measurement units during a time period and outputting a selection signal based on the determination; and selecting information from one of first plurality of quarter-phase measurements based on the selection signal, and outputting the selected information and an indication of the center frequency of the corresponding one of the first plurality of digitally frequency filtered signals (e.g., in some embodiments, this selection is based on the maximum QP amplitude this cycle from the second plurality of digitally frequency filtered signals that corresponds to the narrow-band filters graphed in FIG. 3.2, but is used to select from a corresponding one of the wide-band filters graphed in FIG. 3.1) These embodiments further of the method further include digitally filtering the initial series of digitized signal values to generate a second plurality of digitally frequency filtered signals, wherein each one of the second plurality of digitally frequency filtered signals has a center frequency that is unique among the second plurality of digitally frequency filtered signals, and wherein each one of the second plurality of digitally frequency filtered signals is a wavelet-transformed filtered signal (these digitally frequency filtered signals are for non-tracked components); performing a second plurality of quarter-phase measurements on the second plurality of digitally frequency filtered signals, wherein each of the second plurality of quarter-phase measurements determines and outputs at least two amplitude values and at least four phase-determined time points per full waveform cycle of a corresponding one of the second plurality of digitally frequency filtered signals (these quarter-phase measurements are for non-tracked components).

Some embodiments of the computer-implemented method further includes digitally filtering the initial series of digitized signal values to generate a second plurality of digitally frequency filtered signals, wherein each one of the second plurality of digitally frequency filtered signals has a respective center frequency that corresponds to the respective center frequency of one of the first plurality of digitally frequency filtered signals and a frequency range that is narrower than the frequency range of the respective frequency range of the one of the first plurality of digitally frequency filtered signals, and wherein each one of the second plurality of digitally frequency filtered signals is a wavelet-transformed filtered signal; performing a second plurality of quarter-phase measurements on the second plurality of digitally frequency filtered signals, wherein each of the second plurality of quarter-phase measurements determines and outputs a series of QP objects, wherein each one of the series of QP objects has at least two amplitude values and at least four phase-determined time points per full waveform cycle of a corresponding one of the second plurality of digitally frequency filtered signals; and wherein each one of the first plurality of digitally frequency filtered signals is a wavelet-transformed filtered signal; and wherein the using of the first plurality of digitally frequency filtered signals for detecting and tracking the first frequency component further includes: performing a first plurality of quarter-phase measurements, each of which determines at least two amplitude values and at least four phase-determined time points per full waveform cycle of a corresponding one of the first plurality of digitally frequency filtered signals; determining which one of the second plurality of quarter-phase measurements an amplitude value no lower than did any other one of the second plurality of quarter-phase measurement units during a time period and outputting a selection signal based on the determination; and selecting information from one of first plurality of quarter-phase measurements based on the selection signal, and outputting the selected information and an indication of the center frequency of the corresponding one of the first plurality of digitally frequency filtered signals (e.g., in some embodiments, this selection is based on the maximum QP amplitude this cycle from the second plurality of digitally frequency filtered signals that corresponds to the narrow-band filters graphed in FIG. 3.2, but is used to select from a corresponding one of the wide-band filters graphed in FIG. 3.1).

In some embodiments, the present invention provides a non-transitory computer-readable storage medium having instructions stored thereon, wherein the instructions, when executed by a suitably programmed computer, perform a method that includes: digitally filtering an initial series of digitized signal values in the computer to generate a first plurality of digitally frequency filtered signals, wherein each one of the first plurality of digitally frequency filtered signals has a respective center frequency that is unique among respective center frequencies of the first plurality of digitally frequency filtered signals and a respective frequency range that overlaps the respective frequency range of a closest neighboring one of the first plurality of digitally frequency filtered signals; and using the first plurality of digitally frequency filtered signals for detecting and tracking, in the computer, a first frequency component as that first frequency component's main component moves from one to another frequency range of the first plurality of digitally frequency filtered signals.

In some embodiments of the computer-readable storage medium, the digitally filtering includes wavelet-transforming the initial series of digitized signal values to generate a plurality of wavelet-transformed signals.

In some embodiments of the computer-readable storage medium, the medium further includes instructions to perform any of the other aspects of the methods described herein.

In some embodiments, the present invention provides an apparatus that includes: a computer having a storage device; means for digitally filtering an initial series of digitized signal values in the computer to generate a first plurality of digitally frequency filtered signals, wherein each one of the first plurality of digitally frequency filtered signals has a respective center frequency that is unique among respective center frequencies of the first plurality of digitally frequency filtered signals and a respective frequency range that overlaps the respective frequency range of a closest neighboring one of the first plurality of digitally frequency filtered signals; and means for detecting and tracking, in the computer, a first frequency component as that first frequency component's main component moves from one to another frequency range of the first plurality of digitally frequency filtered signals.

In some embodiments, the present invention provides an apparatus 4000 that includes: a computer having a storage device; a source of an initial series of digitized signal values; a first filter bank that includes a first plurality of digital bandpass filters each operably coupled to the source of digitized signal values and each configured to digitally filter the initial series of digitized signal values, wherein each one of the first plurality of digital bandpass filters has a respective center frequency that is unique among respective center frequencies of the first plurality of digital bandpass filters and a respective frequency range, and wherein each one of the first plurality of digital bandpass filters has an output signal; a first plurality of fractional-phase measurement units that each determines a plurality of amplitude values and a plurality of phase-determined time points per full waveform cycle of the output signal of a corresponding one of the first plurality of digital bandpass filters; and a first frequency-component tracker that uses the plurality of amplitude values from the first plurality of fractional-phase measurement units to detect and track a first tracked frequency component as that first tracked frequency component's frequency moves from one to another frequency range of the first plurality of digital bandpass filters, and to store information regarding the tracked frequency component into the storage device. In some such embodiments, the stored information includes instantaneous frequency and amplitude of the tracked frequency component at each of a first sequence of time points.

In some embodiments of apparatus 4000, each one of the first plurality of digital bandpass filters includes a filter based on a wavelet from a wavelet transform.

In some embodiments of apparatus 4000, the first frequency-component tracker further includes a quarter-phase output unit that determines at least two amplitude values and at least four phase-determined time points per full waveform cycle of the first tracked frequency component, and that outputs a first series of respective data structures that each indicates the at least two amplitude values, the at least four phase-determined time points per respective full waveform cycle of the first tracked frequency component, and a per-time-point instantaneous frequency indication of the first tracked frequency component.

In some embodiments of apparatus 4000, the first plurality of fractional-phase measurement units are quarter-phase measurement units, each of which determines and outputs at least two amplitude values and at least four phase-determined time points per full waveform cycle of an output of the corresponding one of the first plurality of digital bandpass filters. This apparatus further includes a quarter-phase maximum-amplitude determination unit that determines which one of the first plurality of quarter-phase measurement units has an amplitude value no lower than did any other one of the first plurality of quarter-phase measurement units during a time period and that outputs a selection signal based on the determination; and a first selector that selects information from at least one of the first plurality of quarter-phase measurement units based on the selection signal, and outputs the selected information and an indication of the center frequency of the corresponding one or more of the first plurality of digital bandpass filters. In some such embodiments, the center frequency of the corresponding one or more of the first plurality of digital bandpass filters is determined by interpolation. In other embodiments, the quarter-phase maximum-amplitude determination unit further includes a data smoother that smooths amplitude values from each of the first plurality of quarter-phase measurement units before the quarter-phase maximum-amplitude determination unit determines which one of the first plurality of quarter-phase measurement units has the amplitude value no lower than did any other one of the first plurality of quarter-phase measurement units during a time period.

In some embodiments of apparatus 4000, the first quarter-phase bank further includes a data smoother that smooths amplitude values from each of the first plurality of digital bandpass filters before the first quarter-phase bank determines and outputs at least two amplitude values and at least four phase-determined time points per full waveform cycle of an output of the corresponding one of the first plurality of digital bandpass filters.

In some embodiments of apparatus 4000, each one of the first plurality of digital bandpass filters includes a filter based on a wavelet from a wavelet transform, the first plurality of fractional-phase measurement units are quarter-phase measurement units, each of which determines and outputs at least two amplitude values and at least four phase-determined time points per full waveform cycle of an output of the corresponding one of the first plurality of digital bandpass filters, and the first frequency-component tracker further includes: a quarter-phase maximum-amplitude determination unit that determines which one of the first plurality of quarter-phase measurement units had an amplitude value no lower than did any other one of the first plurality of quarter-phase measurement units during a time period and that outputs a selection signal based on the determination; and a selector that selects information from one of first plurality of quarter-phase measurement units based on the selection signal, and outputs the selected information and an indication of the center frequency of the corresponding one of the first plurality of digital bandpass filters.

Some embodiments of apparatus 4000 further include a second plurality of digital bandpass filters, wherein each one of the second plurality of digital bandpass filters has a respective center frequency that corresponds to the respective center frequency of one of the first plurality of digital bandpass filters and a frequency range that is narrower than the frequency range of the respective frequency range of the one of the first plurality of digital bandpass filters, wherein each one of the second plurality of digital bandpass filters includes a filter based on a wavelet from a wavelet transform, and wherein each one of the second plurality of digital bandpass filters has an output signal; a second plurality of quarter-phase measurement units operatively coupled to receive the output signals from the second plurality of digital bandpass filters, wherein each of the second plurality of quarter-phase measurement units determines at least two amplitude values and at least four phase-determined time points per full waveform cycle of a corresponding one of the second plurality of digital bandpass filters; wherein each one of the first plurality of digital bandpass filters includes a filter based on a wavelet from a wavelet transform; and wherein the first plurality of fractional-phase measurement units are quarter-phase measurement units, each of which determines and outputs at least two amplitude values and at least four phase-determined time points per full waveform cycle of an output of the corresponding one of the first plurality of digital bandpass filters; and wherein the first frequency-component tracker further includes: a quarter-phase maximum-amplitude determination unit that determines which one of the second plurality of quarter-phase measurement units had an amplitude value no lower than did any other one of the second plurality of quarter-phase measurement units during a time period and that outputs a selection signal based on the determination; and a selector that selects information from one of first plurality of quarter-phase measurement units based on the selection signal, and outputs the selected information and an indication of the center frequency of the corresponding one of the first plurality of digital bandpass filters.

Some embodiments of apparatus 4000 further include a second plurality of digital bandpass filters, wherein each one of the second plurality of digital bandpass filters has a respective center frequency that corresponds to the respective center frequency of one of the first plurality of digital bandpass filters and a frequency range that is narrower than the frequency range of the respective frequency range of the one of the first plurality of digital bandpass filters, wherein each one of the second plurality of digital bandpass filters includes a filter based on a wavelet from a wavelet transform, and wherein each one of the second plurality of digital bandpass filters has an output signal; a second plurality of quarter-phase measurement units operatively coupled to receive the output signals from the second plurality of digital bandpass filters, wherein each of the second plurality of quarter-phase measurement units determines at least two amplitude values and at least four phase-determined time points per full waveform cycle of a corresponding one of the second plurality of digital bandpass filters, wherein each one of the first plurality of digital bandpass filters includes a filter based on a wavelet from a wavelet transform, and wherein the first plurality of fractional-phase measurement units are quarter-phase measurement units, each of which determines and outputs at least two amplitude values and at least four phase-determined time points per full waveform cycle of an output of the corresponding one of the first plurality of digital bandpass filters; wherein the first frequency-component tracker further includes: a quarter-phase maximum-amplitude determination unit that determines which one of the second plurality of quarter-phase measurement units had an amplitude value no lower than did any other one of the second plurality of quarter-phase measurement units during a time period and that outputs a selection signal based on the determination; a selector that selects information from one of first plurality of quarter-phase measurement units based on the selection signal, and outputs the selected information and an indication of the center frequency of the corresponding one of the first plurality of digital bandpass filters; a third plurality of digital bandpass filters, wherein each one of the third plurality of digital bandpass filters has a center frequency that is unique among the third plurality of digital bandpass filters, wherein each one of the third plurality of digital bandpass filters includes a filter based on a wavelet from a wavelet transform, and wherein each one of the third plurality of digital bandpass filters has an output signal; and a third plurality of quarter-phase measurement units operatively coupled to receive the output signals from the third plurality of digital bandpass filters, wherein each of the third plurality of quarter-phase measurement units determines at least two amplitude values and at least four phase-determined time points per full waveform cycle of a corresponding one of the third plurality of digital bandpass filters. In some such embodiments, the third plurality of digital bandpass filters is not used to track a tracked frequency component.

In some embodiments of apparatus 4000, each one of the first plurality of digital bandpass filters includes a filter based on a wavelet from a wavelet transform; and wherein the first plurality of fractional-phase measurement units are quarter-phase measurement units, each of which determines and outputs at least two amplitude values and at least four phase-determined time points per full waveform cycle of an output of the corresponding one of the first plurality of digital bandpass filters; wherein the first frequency-component tracker further includes: a quarter-phase maximum-amplitude determination unit that determines which one of the first plurality of quarter-phase measurement units had an amplitude value no lower than did any other one of the first plurality of quarter-phase measurement units during a time period and that outputs a selection signal based on the determination; and a selector that selects information from one of first plurality of quarter-phase measurement units based on the selection signal, and outputs the selected information and an indication of the center frequency of the corresponding one of the first plurality of digital bandpass filters. This apparatus further includes a third plurality of digital bandpass filters each operably coupled to the source of digitized signal values, wherein each one of the third plurality of digital bandpass filters has a center frequency that is unique among the third plurality of digital bandpass filters, wherein each one of the third plurality of digital bandpass filters includes a filter based on a wavelet from a wavelet transform, and wherein each one of the third plurality of digital bandpass filters has an output signal; and a third plurality of quarter-phase measurement units operatively coupled to receive the output signals from the third plurality of digital bandpass filters, wherein each of the third plurality of quarter-phase measurement units determines and outputs at least two amplitude values and at least four phase-determined time points per full waveform cycle of a corresponding one of the third plurality of digital bandpass filters. In some such embodiments, the third plurality of digital bandpass filters is not used to track a tracked frequency component.

Some embodiments of apparatus 4000 further include a second plurality of digital bandpass filters, wherein each one of the second plurality of digital bandpass filters has a respective center frequency that corresponds to the respective center frequency of one of the first plurality of digital bandpass filters and a frequency range that is narrower than the frequency range of the respective frequency range of the one of the first plurality of digital bandpass filters, wherein each one of the second plurality of digital bandpass filters includes a filter based on a wavelet from a wavelet transform, and wherein each one of the second plurality of digital bandpass filters has an output signal; a second plurality of quarter-phase measurement units operatively coupled to receive the output signals from the second plurality of digital bandpass filters, wherein each of the second plurality of quarter-phase measurement units determines and outputs a series of QP objects, wherein each one of the series of QP objects has at least two amplitude values and at least four phase-determined time points per full waveform cycle of a corresponding one of the second plurality of digital bandpass filters; and wherein each one of the first plurality of digital bandpass filters includes a filter based on a wavelet from a wavelet transform; wherein each one of the first plurality of digital bandpass filters includes a filter based on a wavelet from a wavelet transform; and wherein the first plurality of fractional-phase measurement units are quarter-phase measurement units, each of which determines and outputs at least two amplitude values and at least four phase-determined time points per full waveform cycle of an output of the corresponding one of the first plurality of digital bandpass filters. In some such embodiments, the first frequency-component tracker further includes: a quarter-phase maximum-amplitude determination unit that determines which one of the second plurality of quarter-phase measurement units had an amplitude value no lower than did any other one of the second plurality of quarter-phase measurement units during a time period and that outputs a selection signal based on the determination; a selector that selects information from one of first plurality of quarter-phase measurement units based on the selection signal, and outputs the selected information and an indication of the center frequency of the corresponding one of the first plurality of digital bandpass filters.

In some embodiments of apparatus 4000, the first frequency-component tracker further includes a fractional-phase output unit that determines a plurality of amplitude values, a plurality of phase-determined time points per full waveform cycle of the first tracked frequency component, and at least one per-unit-time instantaneous-frequency indication based on outputs of selected ones of the first plurality of fractional-phase measurement units for the first tracked frequency component. In some such embodiments, the fractional-phase output unit includes a fractional-phase sequence corrector that corrects a sequence of fractional-phase labels and adjusts corresponding amplitudes and time points of the sequence.

In some embodiments of apparatus 4000, the first frequency-component tracker further includes a data smoother that smooths amplitude values from each of the first plurality of fractional-phase measurement units before the first frequency-component tracker detects and tracks the tracked frequency component as that tracked frequency component's frequency moves from one to another frequency range of the first plurality of digital bandpass filters.

In some embodiments of apparatus 4000, the data smoother that smooths amplitude values from each of the first plurality of fractional-phase measurement units using at least some different numbers of sample values for different ones of the first plurality of fractional-phase measurement units based on the respective center frequencies of the first plurality of digital bandpass filters in order that the smoother includes approximately an equal amount of elapsed time for the number of sample values for the different ones of the first plurality of digital bandpass filters.

In some embodiments of apparatus 4000, the data smoother smooths amplitude values from each of the first plurality of fractional-phase measurement units using low-pass filters.

In some embodiments of apparatus 4000, the data smoother smooths amplitude values from each of the first plurality of fractional-phase measurement units using moving averages.

In some embodiments of apparatus 4000, the first frequency-component tracker further includes: a maximum-amplitude determination unit that determines which one of the first plurality of first plurality of digital bandpass filters had an amplitude value no lower than did any other one of the first plurality of digital bandpass filters during a time period and that outputs a selection signal based on the determination; and a first selector that selects information from at least one of first plurality of digital bandpass filters based on the selection signal, and outputs the selected information and an indication of the center frequency of the selected at least one of the first plurality of digital bandpass filters.

In some embodiments of apparatus 4000, the first frequency-component tracker further includes: a maximum-amplitude determination unit that determines which one of the first plurality of first plurality of digital bandpass filters had an amplitude value no lower than did any other one of the first plurality of digital bandpass filters during a time period and that outputs a selection signal based on the determination; a first selector that selects information from one of first plurality of digital bandpass filters based on the selection signal (i.e., selection based on the filter signals rather than the fractional- or quarter-phase outputs), and outputs the selected information and an indication of the center frequency of the selected one of the first plurality of digital bandpass filters; and a fractional-phase measurement unit that determines and a plurality of phase-determined time points and amplitude values per full waveform cycle of the tracked frequency component.

In some embodiments of apparatus 4000, the first frequency-component tracker further includes: a maximum-amplitude determination unit that determines which one of the first plurality of first plurality of digital bandpass filters had an amplitude value no lower than did any other one of the first plurality of digital bandpass filters during a time period and that outputs a selection signal based on the determination; a first selector that selects information from at least one of first plurality of digital bandpass filters based on the selection signal, and outputs the selected information and an indication of the center frequency of the selected at least one of the first plurality of digital bandpass filters; and a quarter-phase measurement unit that determines at least two amplitude values and at least four phase-determined time points per full waveform cycle of the tracked frequency component.

In some embodiments, the present invention provides a method 4000 that includes: digitally filtering an initial series of digitized signal values in a computer to generate a first plurality of digitally bandpass-filtered signals, wherein each one of the first plurality of digitally bandpass-filtered signals has a respective center frequency that is unique among respective center frequencies of the first plurality of digitally bandpass-filtered signals and a respective frequency range that overlaps the respective frequency range of a closest neighboring one of the first plurality of digitally bandpass-filtered signals; determining a first plurality of fractional-phase amplitude values and a plurality of fractional-phase-determined time points per full waveform cycle of a corresponding one of the first plurality of digitally bandpass filtered signals; using the first plurality of fractional-phase amplitude values for detecting and tracking, in the computer, a first tracked frequency component as that first tracked frequency component's main component moves from one to another frequency range of the first plurality of digitally bandpass-filtered signals; and storing information regarding the tracked frequency component into a storage device. In some such embodiments, the stored information includes instantaneous frequency and amplitude of the tracked frequency component at each of a first sequence of time points.

In some embodiments of method 4000, the digitally filtering includes filtering the initial series of digitized signal values to generate a plurality of wavelet-transformed signals, based on a wavelet from a wavelet transform.

In some embodiments of method 4000, the using of the first plurality of fractional-phase amplitude values for detecting and tracking the first tracked frequency component further includes determining and outputting at least two amplitude values, at least one phase-determined time point per full waveform cycle of the first tracked frequency component, and a per-unit-time center frequency indication of the first tracked frequency component for each respective unit of time of the first tracked frequency component.

In some embodiments of method 4000, the using of the first plurality of fractional-phase amplitude values for detecting and tracking the first frequency component further includes determining at least two amplitude values and at least four phase-determined time points per full waveform cycle of the first tracked frequency component, and outputting a first series of respective quarter-phase data structures that each indicates the at least two amplitude values, the at least four phase-determined time points per respective full waveform cycle of the first tracked frequency component, and a per-cycle center frequency of the first tracked frequency component for the respective full waveform cycle of the first tracked frequency component.

In some embodiments of method 4000, the determining of the first plurality of fractional-phase amplitude values and a plurality of fractional-phase-determined time points includes performing a first plurality of quarter-phase measurements, each of which determines at least two amplitude values and at least four phase-determined time points per full waveform cycle of a corresponding one of the first plurality of digitally bandpass filtered signals, and outputting a resulting plurality of quarter-phase objects, and the using of the first plurality of fractional-phase amplitude values for detecting and tracking the first frequency component further includes: performing a quarter-phase maximum-amplitude determination of which one of the first plurality of quarter-phase objects had an amplitude value no lower than did any other one of the first plurality of quarter-phase objects during a time period and outputting a selection signal based on the determination; and selecting information from one of first plurality of quarter-phase objects based on the selection signal, and outputting the selected information and an indication of the center frequency of the corresponding one of the first plurality of digitally bandpass-filtered signals.

In some embodiments of method 4000, each one of the first plurality of digitally bandpass-filtered signals is a wavelet-bandpass-filtered signal; and the determining of the first plurality of fractional-phase amplitude values and the plurality of fractional-phase-determined time points per full waveform cycle of the corresponding one of the first plurality of digitally bandpass filtered signals further includes performing a first plurality of quarter-phase measurements, each of which determines at least two amplitude values and at least four phase-determined time points per full waveform cycle of a corresponding one of the first plurality of digital bandpass filters. The using of the first plurality of fractional-phase amplitude values for detecting and tracking the first tracked frequency component further includes: determining which one of the first plurality of quarter-phase measurements had an amplitude value no lower than did any other one of the first plurality of quarter-phase measurements during a time period and outputting a selection signal based on the determination; and selecting information from one of first plurality of quarter-phase measurements based on the selection signal, and outputting the selected information and an indication of the center frequency of the corresponding one of the first plurality of digital bandpass filters.

In some embodiments of method 4000, each one of the first plurality of digitally bandpass-filtered signals is a wavelet-transformed filtered signal; and the using of the first plurality of digitally bandpass-filtered signals for detecting and tracking the first frequency component further includes: performing a first plurality of quarter-phase measurements, each of which determines at least two amplitude values and at least four phase-determined time points per full waveform cycle of a corresponding one of the first plurality of digitally bandpass-filtered signals; determining which one of the second plurality of quarter-phase measurements an amplitude value no lower than did any other one of the second plurality of quarter-phase measurement units during a time period and outputting a selection signal based on the determination; and selecting information from one of first plurality of quarter-phase measurements based on the selection signal, and outputting the selected information and an indication of the center frequency of the corresponding one of the first plurality of digitally bandpass-filtered signals.

In some embodiments of method 4000, each one of the first plurality of digitally bandpass-filtered signals is a wavelet-transformed frequency-filtered signal; the determining of the first plurality of fractional-phase amplitude values and the plurality of fractional-phase-determined time points per full waveform cycle of the corresponding one of the first plurality of digitally bandpass filtered signals further includes performing a first plurality of quarter-phase measurements, each of which determines at least two amplitude values and at least four phase-determined time points per full waveform cycle of a corresponding one of the first plurality of digital bandpass filters; and the using of the first plurality of fractional-phase amplitude values for detecting and tracking the first frequency component further includes: determining which one of the first plurality of quarter-phase measurements had an amplitude value no lower than did any other one of the first plurality of quarter-phase measurements during a time period and outputting a selection signal based on the determination; and selecting information (i.e., selection based on QP output) from one of first plurality of quarter-phase measurements based on the selection signal, and outputting the selected information and an indication of the center frequency of the corresponding one of the first plurality of digitally bandpass-filtered signals. The method further includes: digitally filtering the initial series of digitized signal values in a computer to generate a third plurality of digitally bandpass-filtered signals, wherein each one of the third plurality of digitally bandpass-filtered signals has a center frequency that is unique among the third plurality of digitally bandpass-filtered signals and a frequency range that overlaps the frequency range of a closest neighboring one of the third plurality of digitally bandpass-filtered signals, wherein each one of the third plurality of digitally bandpass-filtered signals is a wavelet-transformed frequency-filtered signal; and performing a third plurality of quarter-phase measurements, each of which determines at least two amplitude values and at least four phase-determined time points per full waveform cycle of a corresponding one of the third plurality of digitally bandpass-filtered signals.

Some embodiments of method 4000 further include digitally filtering the initial series of digitized signal values to generate a second plurality of digitally bandpass-filtered signals, wherein each one of the second plurality of digitally bandpass-filtered signals has a respective center frequency that corresponds to the respective center frequency of one of the first plurality of digitally bandpass-filtered signals and a frequency range that is narrower than the frequency range of the respective frequency range of the one of the first plurality of digitally bandpass-filtered signals, and wherein each one of the second plurality of digitally bandpass-filtered signals is a wavelet-transformed filtered signal; and performing a second plurality of quarter-phase measurements on the second plurality of digitally bandpass-filtered signals, wherein each of the second plurality of quarter-phase measurements determines at least two amplitude values and at least four phase-determined time points per full waveform cycle of a corresponding one of the second plurality of digitally bandpass-filtered signals. In some such embodiments, each one of the first plurality of digitally bandpass-filtered signals is a wavelet-transformed filtered signal; and the using of the first plurality of digitally bandpass-filtered signals for detecting and tracking the first frequency component further includes: performing a first plurality of quarter-phase measurements, each of which determines at least two amplitude values and at least four phase-determined time points per full waveform cycle of a corresponding one of the first plurality of digitally bandpass-filtered signals; determining which one of the second plurality of quarter-phase measurements an amplitude value no lower than did any other one of the second plurality of quarter-phase measurement units during a time period and outputting a selection signal based on the determination; and selecting information from one of first plurality of quarter-phase measurements based on the selection signal, and outputting the selected information and an indication of the center frequency of the corresponding one of the first plurality of digitally bandpass-filtered signals. In some such embodiments, the method further includes: digitally filtering the initial series of digitized signal values to generate a third plurality of digitally bandpass-filtered signals, wherein each one of the third plurality of digitally bandpass-filtered signals has a center frequency that is unique among the third plurality of digitally bandpass-filtered signals, and wherein each one of the third plurality of digitally bandpass-filtered signals is a wavelet-transformed filtered signal; and performing a third plurality of quarter-phase measurements on the third plurality of digitally bandpass-filtered signals, wherein each of the third plurality of quarter-phase measurements determines and outputs at least two amplitude values and at least four phase-determined time points per full waveform cycle of a corresponding one of the third plurality of digitally bandpass-filtered signals.

Some embodiments of method 4000 further include digitally filtering the initial series of digitized signal values to generate a second plurality of digitally bandpass-filtered signals, wherein each one of the second plurality of digitally bandpass-filtered signals has a respective center frequency that corresponds to the respective center frequency of one of the first plurality of digitally bandpass-filtered signals and a frequency range that is narrower than the frequency range of the respective frequency range of the one of the first plurality of digitally bandpass-filtered signals, and wherein each one of the second plurality of digitally bandpass-filtered signals is a wavelet-transformed filtered signal; performing a second plurality of quarter-phase measurements on the second plurality of digitally bandpass-filtered signals, wherein each of the second plurality of quarter-phase measurements determines and outputs a series of QP objects, wherein each one of the series of QP objects has at least two amplitude values and at least four phase-determined time points per full waveform cycle of a corresponding one of the second plurality of digitally bandpass-filtered signals, wherein each one of the first plurality of digitally bandpass-filtered signals is a wavelet-transformed filtered signal. In some such embodiments, the using of the first plurality of digitally bandpass-filtered signals for detecting and tracking the first frequency component further includes: performing a first plurality of quarter-phase measurements, each of which determines at least two amplitude values and at least four phase-determined time points per full waveform cycle of a corresponding one of the first plurality of digitally bandpass-filtered signals; determining which one of the second plurality of quarter-phase measurements had an amplitude value no lower than did any other one of the second plurality of quarter-phase measurement units during a time period and outputting a selection signal based on the determination; and selecting information (selection based on QP output) from one of first plurality of quarter-phase measurements based on the selection signal, and outputting the selected information and an indication of the center frequency of the corresponding one of the first plurality of digitally bandpass-filtered signals.

In some embodiments of method 4000, the using of the first plurality of digitally bandpass-filtered signals for detecting and tracking the first frequency component further includes: determining which one of the first plurality of first plurality of digitally bandpass-filtered signals had an amplitude value no lower than did any other one of the first plurality of digitally bandpass-filtered signals during a time period and outputting a selection signal based on the determination; and selecting information from one of first plurality of digitally bandpass-filtered output signals based on the selection signal, and outputting the selected information and an indication of the center frequency of the selected one of the first plurality of digitally bandpass-filtered signals.

In some embodiments of method 4000, the using of the first plurality of digitally bandpass-filtered signals for detecting and tracking the first frequency component further includes: determining which one of the first plurality of first plurality of digitally bandpass-filtered signals had an amplitude value no lower than did any other one of the first plurality of digitally bandpass-filtered signals during a time period and outputting a selection signal based on the determination; selecting information from one of first plurality of digitally bandpass-filtered signals based on the selection signal, and outputting the selected information and an indication of the center frequency of the selected one of the first plurality of digitally bandpass-filtered signals; and performing a fractional-phase measurement that determines at least two amplitude values and at least one phase-determined time point per full waveform cycle of the tracked frequency component.

In some embodiments of method 4000, the using of the first plurality of digitally bandpass-filtered signals for detecting and tracking the first frequency component further includes: determining which one of the first plurality of first plurality of digitally bandpass-filtered signals had an amplitude value no lower than did any other one of the first plurality of digitally bandpass-filtered signals during a time period and outputting a selection signal based on the determination; selecting information from one of first plurality of digitally bandpass-filtered signals based on the selection signal, and outputs the selected information and an indication of the center frequency of the selected one of the first plurality of digitally bandpass-filtered signals; and performing a quarter-phase measurement that determines and outputs at least two amplitude values and at least four phase-determined time points per full waveform cycle of the tracked frequency component.

In some embodiments, the present invention provides a non-transitory computer-readable storage medium having instructions stored thereon, wherein the instructions, when executed by a suitably programmed computer, perform a method that includes digitally filtering an initial series of digitized signal values in a computer to generate a first plurality of digitally bandpass-filtered signals, wherein each one of the first plurality of digitally bandpass-filtered signals has a respective center frequency that is unique among respective center frequencies of the first plurality of digitally bandpass-filtered signals and a respective frequency range that overlaps the respective frequency range of a closest neighboring one of the first plurality of digitally bandpass-filtered signals; determining a first plurality of fractional-phase amplitude values and a plurality of fractional-phase-determined time points per full waveform cycle of a corresponding one of the first plurality of digitally bandpass filtered signals; using the first plurality of fractional-phase amplitude values for detecting and tracking, in the computer, a first tracked frequency component as that first tracked frequency component's main component moves from one to another frequency range of the first plurality of digitally bandpass-filtered signals; and storing information regarding the tracked frequency component into a storage device. In some such embodiments, the stored information includes instantaneous frequency and amplitude of the tracked frequency component at each of a first sequence of time points. In some embodiments, the digitally filtering includes wavelet-transforming the initial series of digitized signal values to generate a plurality of wavelet-transformed signals.

In some embodiments, the present invention provides a non-transitory computer-readable storage medium having instructions stored thereon, wherein the instructions, when executed by a suitably programmed computer, perform any of the methods described herein, including subsets of any method and combinations of any portions of the methods.

In some embodiments, the present invention provides an apparatus that includes a computer having a storage device; means for digitally filtering an initial series of digitized signal values in a computer to generate a first plurality of digitally bandpass-filtered signals, wherein each one of the first plurality of digitally bandpass-filtered signals has a respective center frequency that is unique among respective center frequencies of the first plurality of digitally bandpass-filtered signals and a respective frequency range that overlaps the respective frequency range of a closest neighboring one of the first plurality of digitally bandpass-filtered signals; means for determining a first plurality of fractional-phase amplitude values and a plurality of fractional-phase-determined time points per full waveform cycle of a corresponding one of the first plurality of digitally bandpass filtered signals; means for using the first plurality of fractional-phase amplitude values for detecting and tracking, in the computer, a first tracked frequency component as that first tracked frequency component's main component moves from one to another frequency range of the first plurality of digitally bandpass-filtered signals; and means for storing information regarding the tracked frequency component into a storage device. In some such embodiments, the stored information includes instantaneous frequency and amplitude of the tracked frequency component at each of a first sequence of time points.

It is to be understood that the above description is intended to be illustrative, and not restrictive. Although numerous characteristics and advantages of various embodiments as described herein have been set forth in the foregoing description, together with details of the structure and function of various embodiments, many other embodiments and changes to details will be apparent to those of skill in the art upon reviewing the above description. The scope of the invention should be, therefore, determined with reference to the appended claims, along with the full scope of equivalents to which such claims are entitled. In the appended claims, the terms "including" and "in which" are used as the plain-English equivalents of the respective terms "comprising" and "wherein," respectively. Moreover, the terms "first," "second," and "third," etc., are used merely as labels, and are not intended to impose numerical requirements on their objects.

What is claimed is:

1. An apparatus comprising:
a computer having a storage device;
a source of an initial series of digitized signal values;
a first filter bank that includes a set of digital bandpass filters per octave of frequency, each digital bandpass filter of each set of digital bandpass filters operably coupled to the source of the initial series of digitized signal values and each digital bandpass filter configured to digitally filter the initial series of digitized signal values, wherein each set of digital bandpass filters has a respective center frequency that is unique among respective center frequencies of all sets of digital bandpass filters, and wherein each set of digital bandpass filters has a respective filter output signal;
a first fractional-phase-unit bank that includes a respective fractional-phase unit corresponding to each set of digital bandpass filters, and configured to receive the respective filter output signal and to generate a respective fractional phase representation for each successive time period; and
a state constructor that constructs a plurality of successive states containing information derived from the respective fractional phase representations of the first fractional-phase-unit bank.

2. The apparatus of claim 1, wherein each set of digital bandpass filters includes a filter based on a wavelet transform.

3. The apparatus of claim 1, further comprising:
a first frequency-component tracker that further includes:
a fractional-phase output unit that determines a plurality of amplitude values and a plurality of phase-determined time points per full waveform cycle of a first tracked frequency component, and that outputs a first series of respective data structures that each indicates the plurality of amplitude values, the plurality of phase-determined time points per respective full waveform cycle of the first tracked frequency component, and a per-time-point instantaneous frequency indication of the first tracked frequency component.

4. The apparatus of claim 1, wherein each respective fractional-phase unit of the first fractional-phase-unit bank further includes a respective fractional-phase measurement unit that determines and outputs a plurality of amplitude values and a plurality of phase-determined time points per full waveform cycle of an output of the corresponding respective set of digital bandpass filters;
a respective fractional-phase maximum-amplitude determination unit that determines which one of the fractional-phase measurement units has an amplitude value no lower than any other one of a plurality of fractional-phase measurement units during a time period and that outputs a selection signal based on the determination; and wherein the apparatus further includes:
a first selector that selects information from at least one of the respective fractional-phase measurement units based on the selection signal, and outputs the selected information and an indication of the respective center frequency of the corresponding at least one set of digital bandpass filters, wherein the center frequency of the corresponding at least one set of digital bandpass filters is determined by interpolation.

5. The apparatus of claim 4, wherein the fractional-phase maximum-amplitude determination unit further includes a data smoother that smooths amplitude values from each of the first plurality of fractional-phase measurement units before the fractional-phase maximum-amplitude determination unit determines which one of the first plurality of fractional-phase measurement units has the amplitude value no lower than did any other one of the first plurality of fractional-phase measurement units during a time period.

6. The apparatus of claim 1, wherein each set of digital bandpass filters includes a first bandpass filter and a second, neighboring, bandpass filter, wherein the first bandpass filter has a maximum response at the respective center frequency of the first bandpass filter, wherein the second bandpass filter has a maximum response at the respective center frequency of the second bandpass filter, and wherein the first bandpass filter and the second bandpass filter have a cross-over point that is about −0.1 dB from either maximum response.

7. The apparatus of claim 1, wherein the first filter bank includes at least four digital bandpass filters per octave of frequency each having a different center frequency.

8. The apparatus of claim 1, wherein the first filter bank includes at least eight digital bandpass filters per octave of frequency each having a different center frequency.

9. The apparatus of claim 1, wherein the first filter bank includes at least sixteen digital bandpass filters per octave of frequency each having a different center frequency.

10. A computer-implemented method comprising:
sensing a quasi-periodic signal and generating an initial series of digitized signal values based on the sensed signal;
digitally filtering the initial series of digitized signal values in a computer to generate a first set of digitally bandpass-filtered signals per octave of frequency, wherein each first set of digitally bandpass-filtered signals has a respective center frequency that is unique among respective center frequencies of all first sets of digitally bandpass-filtered signals and a respective frequency range that overlaps the respective frequency range of a closest neighboring first set of digitally bandpass-filtered signals;
determining a plurality of fractional phase representations, each of the plurality of fractional phase representations including one or more amplitude values and a plurality of phase-determined time points per full waveform cycle of each respective first set of digitally bandpass-filtered signals; and
outputting a first series of respective fractional-phase data states, wherein each of the first series of respective fractional-phase data states indicates the one or more amplitude values and the plurality of phase-determined time points per respective full waveform cycle of the respective first set of digitally bandpass-filtered signals.

11. The computer-implemented method of claim 10, wherein the digitally filtering includes filtering the initial series of digitized signal values to generate a plurality of wavelet-transformed signals, based on a wavelet transform.

12. The computer-implemented method of claim 10, further comprising:
detecting and tracking of a first frequency component by determining a plurality of amplitude values and a plurality of phase-determined time points per full waveform cycle of the first tracked frequency component, and outputting a first series of respective fractional-phase data structures that each indicates the plurality of amplitude values, the plurality of phase-determined time points per respective full waveform cycle of the first tracked frequency component, and a per-cycle center frequency of the first tracked frequency component for the respective full waveform cycle of the first tracked frequency component.

13. The computer-implemented method of claim 10, wherein the determining of the plurality of fractional phase representations further includes:
performing a first plurality of fractional-phase measurements, each of which determines a plurality of amplitude values and a plurality of phase-determined time points per full waveform cycle of a corresponding first set of digitally bandpass-filtered signals;
wherein each first set of digitally bandpass-filtered signals is a wavelet-bandpass-filtered signal; and
wherein the method further includes detecting and tracking of a first tracked frequency component, which further includes:
determining which one of the first plurality of fractional-phase measurements had an amplitude value no lower than did any other one of the first plurality of fractional-phase measurements during a time period and outputting a selection signal based on the determination; and
selecting information from one of first plurality of fractional-phase measurements based on the selection signal, and outputting the selected information and an indication of the center frequency of the corresponding first set of digitally bandpass-filtered signals.

14. The computer-implemented method of claim 13,
wherein each first set of digitally bandpass-filtered signals is a wavelet-transformed filtered signal; and
wherein the detecting and tracking of the first tracked frequency component further includes:
performing a first plurality of fractional-phase measurements, each of which determines a plurality of amplitude values and a plurality of phase-determined time points per full waveform cycle of a corresponding first set of digitally bandpass-filtered signals;
determining which one of the first plurality of fractional-phase measurements has an amplitude value no lower than did any other one of the first plurality of fractional-phase measurements during a time period and outputting a selection signal based on the determination; and
selecting information from one of the first plurality of fractional-phase measurements based on the selection signal, and outputting the selected information and an indication of the center frequency of the corresponding first set of digitally bandpass-filtered signals.

15. The computer-implemented method of claim 10, wherein each first set of digitally bandpass-filtered signals includes a first bandpass-filtered signal and a second, neighboring, bandpass-filtered signal, wherein the first bandpass-filtered signal has a maximum response at the respective center frequency of the first bandpass-filtered signal, wherein the second bandpass-filtered signal has a maximum response at the respective center frequency of the second bandpass-filtered signal, and wherein the first bandpass-filtered signal and the second bandpass-filtered signal have a cross-over point that is about −0.1 dB from either maximum response.

16. The computer-implemented method of claim 10, further comprising:
performing a first plurality of fractional-phase measurements, each of which determines a plurality of amplitude values and a plurality of phase-determined time points per full waveform cycle of a corresponding first set of digitally bandpass-filtered signals, wherein each first set of digitally bandpass-filtered signals is a wavelet-transformed frequency-filtered signal, wherein the detecting and tracking of the first frequency component further includes:
determining which one of the first plurality of fractional-phase measurements had an amplitude value no lower than did any other one of the first plurality of fractional-phase measurements during a time period and outputting a selection signal based on the determination; and selecting information from one of first plurality of fractional-phase measurements based on the selection signal, and outputting the selected information and an indication of the center frequency of the corresponding first set of digitally bandpass-filtered signals;

digitally filtering the initial series of digitized signal values in a computer to generate a second set of digitally bandpass-filtered signals, wherein each second set of digitally bandpass-filtered signals has a center frequency that is unique among all second sets of digitally bandpass-filtered signals and a frequency range that overlaps the frequency range of a closest neighboring second set of digitally bandpass-filtered signals, wherein each second set of digitally bandpass-filtered signals is a wavelet-transformed frequency-filtered signal; and performing a second plurality of fractional-phase measurements, each of which determines a plurality of amplitude values and a plurality of phase-determined time points per full waveform cycle of a corresponding second set of digitally bandpass-filtered signals.

17. The computer-implemented method of claim 10, wherein the initial series of digitized signal values represent certain types of internet messages, wherein the method further includes:

tracking and recording a particular frequency component of the certain types of internet messages; and analyzing the recorded particular frequency component to help predict a human activity.

18. A non-transitory computer-readable storage medium having instructions stored thereon, wherein the instructions, when executed by a suitably programmed computer, perform a method comprising:

digitally filtering an initial series of digitized signal values in a computer to generate a set of digitally bandpass-filtered signals per octave of frequency, wherein each set of digitally bandpass-filtered signals has a respective center frequency that is unique among respective center frequencies of all sets of digitally bandpass-filtered signals and a respective frequency range that overlaps the respective frequency range of a closest neighboring set of digitally bandpass-filtered signals;

determining a plurality of fractional phase representations, each of the plurality of fractional phase representations including one or more amplitude values and a plurality of phase-determined time points per full waveform cycle of each respective set of digitally bandpass-filtered signals; and outputting a first series of respective fractional-phase data states, wherein each of the first series of respective fractional-phase data states indicates the one or more amplitude values and the plurality of phase-determined time points per respective full waveform cycle of the respective set of digitally bandpass-filtered signals.

19. The non-transitory computer-readable storage medium of claim 18, wherein the initial series of digitized signal values represent a seismic signal, and wherein the instructions, when executed by the computer, cause the method to further include:

tracking and recording a particular frequency component of the seismic signal; and analyzing the recorded particular frequency component to help predict earthquakes.

20. The computer-implemented method of claim 10, wherein the digitally filtering of the initial series of digitized signal values generates at least four digitally bandpass-filtered signals per octave of frequency, and wherein each of the at least four digitally bandpass-filtered signals per octave of frequency has a different center frequency.

* * * * *